United States Patent [19]

Ternansky

[11] Patent Number: 4,716,232

[45] Date of Patent: Dec. 29, 1987

[54] 1-(VINYL PHOSPHONATE ADDUCT) PYRAZOLIDINONES

[75] Inventor: Robert J. Ternansky, Indianapolis, Ind.

[73] Assignee: Eli Lilly and Company, Indianapolis, Ind.

[21] Appl. No.: 862,913

[22] Filed: May 14, 1986

[30] Foreign Application Priority Data

Apr. 28, 1986 [EP] European Pat. Off. ........ 86303174.6

[51] Int. Cl.$^4$ ............................ C07F 9/58; C07F 9/65
[52] U.S. Cl. ................................ 548/112; 544/214; 544/228; 544/232; 544/243; 546/14; 546/24; 548/110
[58] Field of Search .................. 548/112, 110; 546/24, 546/14; 544/214, 232, 243, 228

[56] References Cited

FOREIGN PATENT DOCUMENTS

| 23636 | 2/1981 | European Pat. Off. |
| 64058 | 5/1968 | German Democratic Rep. |
| 119868 | 1/1975 | German Democratic Rep. |
| 1472052 | 4/1977 | United Kingdom |
| 2073740A | 10/1981 | United Kingdom |
| 1377596 | 12/1984 | United Kingdom |

OTHER PUBLICATIONS

M. Ueda, M. Funayama and Y. Imai, *J. Polymer Science Polym. Chem. Ed.*, 15, pp. 1629–1635, (1977).

M. A. Breger, *Antibioki*, 16, pp. 26–27, (1961), (Plus English Translation).

H. Dorn and A. Otto, *Angew. Chem. Int. Ed. Engl.*, 7, pp. 214–215, (1968).

H. Dorn and A. Otto, *Chem. Ber.*, 101, pp. 3287–3301, (1968), (plus English translation).

H. Dorn and A. Zubek, *Z. Chem.*, 8, pp. 218–219, (1968).

*Primary Examiner*—Richard L. Raymond
*Attorney, Agent, or Firm*—Paul C. Steinhardt; Leroy Whitaker

[57] ABSTRACT

1-(Vinyl phosphonate adduct) pyrazolidinones are intermediates to bicyclic pyrazolidinone antimicrobial compounds.

18 Claims, No Drawings

1-(VINYL PHOSPHONATE ADDUCT) PYRAZOLIDINONES

SUMMARY OF THE INVENTION

The invention is directed to intermediate compounds of the formula

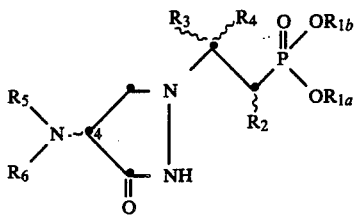

wherein $R_1{}^a$, $R_1{}^b$, $R_2$, $R_3$, $R_4$, $R_5$, and $R_6$ have the meanings defined below.

The present intermediate compounds are precursors of bicyclic pyrazolidinone antibiotics.

DETAILED DESCRIPTION OF THE INVENTION

I. The INVENTION IN GENERAL; DEFINITION OF TERMS

The present invention embraces compound of the Formula I:

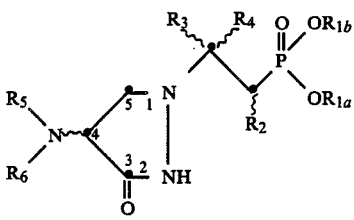

I

The compounds of Formula I are 4-(substituted amino)-3-oxo-1-(vinyl phosphonate adduct)-1,2-pyrazolidinones, which for brevity's sake will be referred to as a "vinyl phosphonate adduct pyrazolidinone" compound, or, more simply, "vinyl phosphonate adduct" compound, in the following Specification. The numbering system for the pyrazolidinone ring is also denoted in Formula I.

In the above Formula, the undulating lines connecting $R_2$, $R_3$, and $R_4$ to the substituent bonded to the oneposition and the nitrogen atom to the four position of the ring system indicate that the stereochemistry at these positions could be independently in the R or S configuration. Furthermore, the Formula represents the compounds of the invention in all of the possible enantiomeric and diastereomeric mixtures.

In the above Formula I:

$R_{1a}$ and $R_{1b}$ are the same or different and are $C_1$ to $C_6$ alkyl or phenyl;

$R_2$ is is hydrogen, halo, $C_1$ to $C_6$ alkyl, $C_1$ to $C_6$ substituted alkyl, perfluoro $C_2$ to $C_4$ alkyl, $C_7$ to $C_{12}$ arylalkyl, $C_7$ to $C_{12}$ substituted arylalkyl, phenyl, substituted phenyl, a heterocyclic ring, nitro or cyano; a group of the formula

—$CX_3$ wherein X is fluoro, chloro, bromo or iodo; a group of the formula $$\overset{(O)_z}{\underset{\|}{-S-R_7}}$$

wherein Z is 0, 1 or 2 and $R_7$ is $C_1$ to $C_6$ alkyl, $C_1$ to $C_6$ substituted alkyl, phenyl, substituted phenyl, $C_7$ to $C_{12}$ arylalkyl, $C_7$ to $C_{12}$ substituted arylalkyl or a heterocyclic ring; a group of the formula

—$COR_8$ wherein $R_8$ is hydrogen, $C_1$ to $C_6$ alkyl, $C_1$ to $C_6$ substituted alkyl, perfluoro $C_2$ to $C_4$ alkyl, $C_7$ to $C_{12}$ arylalkyl, $C_7$ to $C_{12}$ substituted arylalkyl, phenyl, substituted phenyl, amino, (monosubstituted)amino or (disubstituted)amino; a group of the formula

—$COOR_9$ wherein $R_9$ is $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl, a carboxy-protecting group or a non-toxic, metabolically-labile ester-forming group; a group of the formula

—$PO_3(R_{10})_2$ wherein $R_{10}$ is $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, or substituted phenyl; or a group of the formula —$CH_2$—S—Heterocyclic ring;

$R_3$ and $R_4$ are the same or different and are hydrogen, $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl or a group of the formula

—$COOR_{11}$ wherein $R_{11}$ has the same definition as $R_9$;
$R_5$ and $R_6$ are:
 (1) each hydrogen;
 (2) taken together and form a phthalimido group; or
 (3) different and are either hydrogen or an amino-protecting group;
or a pharmaceutically-acceptable salt thereof.

In the above Formula I, the term "$C_1$ to $C_6$ alkyl" denotes such radicals as methyl, ethyl, n-propyl, isopropyl, n-butyl, sec-butyl, tert-butyl, amyl, tertamyl, hexyl and the like. The preferred "$C_1$ to $C_6$ alkyl" group is methyl.

The term "$C_1$ to $C_6$ substituted alkyl" denotes the above $C_1$ to $C_6$ alkyl groups that are substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(nbutyl), 2-amino(iso-propyl), 2-carbamoyloxyethyl and the like. A preferred group of examples within the above "$C_1$ to $C_6$ substituted alkyl" group includes the substituted methyl group, in other words, a methyl group substituted by the same substituents as the "$C_1$ to $C_6$ substituted alkyl" group. Examples of the substituted methyl group include groups such as protected hydroxymethyl, (e.g., tetrahydropyranyloxymethyl), acetoxymethyl, carbamoyloxymethyl, chloromethyl, bromomethyl and iodomethyl.

The term "$C_1$ to $C_4$ alkoxy" as used herein denotes groups such as methoxy, ethoxy, n-propoxy, isopropoxy, n-butoxy, t-butoxy and like groups. The term "$C_1$ to $C_7$ acyloxy" denotes herein groups such as formyloxy, acetoxy, propionyloxy, butyryloxy, pentanoyloxy, hexanoyloxy, heptanoyloxy, and the like.

Examples of the term "perfluoro $C_2$ to $C_4$ alkyl" include perfluoroethyl, perfluoro n-propyl, perfluoro iso-propyl, perfluoro n-butyl, perfluoro sec-butyl and the like.

The term "substituted phenyl" specifies a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino).

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, and the like; a mono- or di(hydroxy)phenyl group such as 4-hydroxyphenyl, 3-hydroxyphenyl, 2,4-dihydroxyphenyl, the protected-hydroxy derivatives thereof, and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl, and the like; a mono- or di(alkoxy)phenyl group, for example, 2,6-dimethoxyphenyl, 4-methoxyphenyl, 3-ethoxyphenyl, 4-(iso-propoxy)phenyl, 4-(t-butoxy)phenyl, 3-ethoxy-4-methoxyphenyl, and the like; 3- or 4- trifluoromethylphenyl; a mono- or dicarboxyphenyl or (protected carboxy)phenyl group such as 4-carboxyphenyl or 2,4-di(-protected carboxy)phenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like. Preferred substituted phenyl groups include the 2- and 3-trifluoromethylphenyl, the 4-hydroxyphenyl, the 2-aminomethylphenyl, and the 3-(N-(methylsulfonylamino))phenyl groups.

The terms "halo" and "halogen" refer to the fluoro, chloro, bromo or iodo groups.

The term "$C_7$ to $C_{12}$ arylalkyl" denotes a $C_1$ to $C_6$ alkyl group substituted at any position by a phenyl ring. Examples of such a group include phenyl methyl (benzyl), 2-phenylethyl, 3-phenyl-(n-propyl), 4-phenylhexyl, 3-phenyl-(n-amyl), 3-phenyl-(sec-butyl), and the like. A preferred group is the benzyl group.

The term "$C_7$ to $C_{12}$ substituted arylalkyl" denotes a $C_7$ to $C_{12}$ arylalkyl group substituted on the $C_1$ to $C_6$ alkyl portion with one or two groups chosen from halogen, hydroxy, protected hydroxy, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or a N-(methylsulfonylamino) group. As before, when either the $C_1$ to $C_6$ alkyl portion or the phenyl portion or both are disubstituted, the substituents can be the same or different.

Examples of the term "$C_7$ to $C_{12}$ substituted arylalkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomethyl phenyl)-3-(aminomethyl)(n-pentyl), and the like.

The term "(monosubstituted)amino" refers to an amino group with one substituent chosen from the group consisting of phenyl, substituted phenyl, $C_1$ to $C_6$ alkyl, and $C_7$ to $C_{12}$ arylalkyl, wherein the latter three substituent terms are as defined above.

The term "(disubstituted)amino" refers to amino groups with two substituents chosen from the group consisting of phenyl, substituted phenyl, $C_1$ to $C_6$ alkyl, and $C_7$ to $C_{12}$ arylalkyl, wherein the latter three substituent terms are as described above. The two substituents can be the same or different.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, barium and calcium); ammonium; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used in the specification refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2', 4,4'-tetramethoxybenzhydryl, t-butyl, t-amyl, trityl, 4-methoxytrityl, 4,4'-dimethoxytrityl, 4,4', 4''-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the vinyl phosphonate adduct and can be removed at the appropriate point without disrupting the remainder of the molecule. (In particular, it is important not to subject the carboxy-protected vinyl phosphonate adducts to strong nucleophilic bases or reductive conditions employing highly activated metal catalysts such as Raney nickel. Such harsh removal conditions are also to be avoided when removing amino-protecting groups and hydroxy-protecting groups, discussed below.) A preferred carboxylic acid protecting group is the allyl group. Similar carboxy-protecting groups used in the cephalosporin, penicillin and peptide arts can also be used to protect carboxy group substituents of the instant pyrazolidinones. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, $\beta$-methoxyethoxymethyl, methylthiomethyl, t-butyl, t-amyl, trityl, 4-methoxytrityl, 4,4'-dimethoxytrityl, 4,4', 4''-trimethoxytrityl, benzyl, allyl, trimethylsilyl, (t-butyl)dimethylsilyl, 2,2,2-trichloroethoxycarbonyl groups and the like.

The species of hydroxy-protecting groups is not critical so long as the derivatized hydroxyl group is stable to the conditions of subsequent reaction(s) and can be removed at the appropriate point without disrupting either the pyrazolidinone ring or any of the appended substituents.

Further examples of hydroxy-protecting groups are described by C. B. Reese and E. Haslam, "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. Some preferred hydroxy-protecting groups are the trityl group and the tetrahydropyranyl group. The related term "protected hydroxy" denotes a hydroxy group bonded to one of the above hydroxyprotecting groups.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl, and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)-ethoxycarbonyl, 2-(triphenylphosphino)-ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the conditions of subsequent reaction(s) on other positions of the vinyl phosphonate adduct and can be removed at the appropriate point without disrupting the remainder of the subsequent product molecule(s) Preferred amino-protecting groups are the allyloxycarbonyl, the t-butoxycarbonyl, and the trityl groups. Similar amino-protecting groups used in the cephalosporin, penicillin and peptide art are also embraced by the above term. Further examples of groups referred to by the above term are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

The term "non-toxic, metabolically-labile ester-forming group" refers to those biologically active ester forms which induce increased blood levels and prolong the efficacy of the corresponding non-esterified forms of the compounds. Such ester groups include the lower alkoxymethyl groups, for example, methoxymethyl, ethoxymethyl, iso-propoxymethyl and the like; the α-($C_1$ to $C_4$)alkoxyethyl groups, for example methoxyethyl, ethoxyethyl, propoxyethyl, iso-propoxyethyl, and the like; the 2-oxo-1,3-dioxolen-4-ylmethyl groups, such as 5-methyl-2-oxo-1,3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, α-acetoxymethyl, and the like; the ethoxycarbonyl-1-methyl group; the α-acyloxy-α-substituted methyl groups, for example α-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred.

Furthermore, the above optionally substituted five-membered or six-membered rings can optionally be fused to a aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

A preferred group of examples of the above heterocyclic rings, when $R_2$ is either a heterocyclic thiomethyl group or simply a heterocyclic group, are 5-membered ring systems containing a sulfur or oxygen atom and one to three nitrogen atoms. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl and tetrazolyl, preferably 1H-tetrazol-5-yl. A preferred group of examples of benzo-fused derivatives are, in particular, benzoxazol-2-yl, benzthiazol-2-yl and benzimidazol-2-yl.

Further specific examples of the above heterocyclic ring systems are 6-membered ring systems containing one to three nitrogen atoms. Such examples include pyridyl, such as pyrid-2-yl, pyrid-3-yl and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides, and the pyridyl, pyrimid-2-yl, pyrimid-4-yl, pyridazinyl and the 1,3,4-triazin-2-yl radicals, are a preferred group.

The substituents for the optionally substituted heterocyclic ring systems, and further examples of the 5- and 6- membered ring systems discussed above, are found in W. Dürckheimer et al., U.S. Pat. No. 4,278,793, issued July 14, 1981, columns 9 through 21 and columns 33 through 188, herein incorporated by reference. (In columns 33 through 188, examples of the term "heterocyclic ring" are included in the heterocyclic thiomethyl groups listed under heading "A".)

A particularly preferred group of examples of the term "heterocyclic ring", when the ring is directly bonded to the 1-substituent or part of a heterocyclic thiomethyl group, is 1,3-thiazol-2-yl, 4-(protected carboxymethyl)-5-methyl-1,3-thiazol-2-yl, 1,2,4-thiadiazol-5-yl, 3-methyl-1,2,4-thiadiazol-5-yl 1,3,4-triazol-5-yl, 2-methyl-1,3,4-triazol-5-yl, 2-hydroxy-1,3,4-triazol-5-yl, 2-(protected carboxy)-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiodiozol-5-yl, 2-thiol-1,3,4-thiadiazol-5-yl, 2-(methylthio)-1,3,4-thiadiazol-5-yl, 2-amino-1,3,4-thiadiozol-5-yl, 1H-tetrazol-5-yl, 1-methyl-1H-tetrazol-5-yl, 1-(1-(dimethylamino)eth-2-yl)-1H-tetrazol-5-yl, 1-(protected carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3triazol-5-yl, 4-methyl-1,2,3-triazol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-astriazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methylas-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo-[1,5-b]pyridazin-6-yl.

A most preferred group of examples of the term "heterocyclic ring" is 4-(protected carboxymethyl)-5-methyl-1,3-thiazol-2-yl, 1,3,4-triazol-5-yl, 2-methyl- 1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(protected carboxymethyl)-1H-tetrazol-5-yl, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-astriazin-3-yl, tetrazolo[1,5-b]pyridazin-6-yl, and 8-aminotetrazolo[1,5-b]pyridazin-6-yl.

In the above Formula I, when $R_2$ is a group of the formula

wherein $R_7$ is a heterocyclic group, examples of such groups are 1,3-thiazol-2-ylthio, 4-(protected carboxymethyl)-5-methyl-1,3-thiazol-2-ylthio, 1,2,4-thiadiazol-5-ylthio, 3-methyl-1,2,4-thiadiazol-5-ylthio, 1,3,4-triazol-5-ylthio, 2-methyl-1,3,4-triazol-5-ylthio, 2-hydroxy-1,3,4-triazol-5-ylthio, 2-(protected carboxy)-4-methyl-1,3,4-triazol-5-ylthio, 1,3-oxazol-2-ylthio, 1,3,4-oxadiazol-5-ylthio, 2-methyl-1,3,4-oxadiazol-5-ylthio, 2-(hydroxymethyl)-1,3,4-oxadiazol-5-ylthio, 1,2,4-oxadiazol-5-ylthio, 1,2,4-oxadiazol-5-ylthio, 1,3,4-thiadiazol-5-ylthio, 2-methyl-1,3,4-thiadiazol- 5-ylthio, 2-thiol-1,3,4-thiadiazol-5-ylthio, 2-(methylthio)-1,3,4-thiadiazol-5-ylthio, 2-amino-1,3,4-thiadiazol-5-ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(protected carboxymethyl)-1H-tetrazol-5-ylthio, 1-(methylsulfonic acid)-1H-tetrazol-5-ylthio, 1-(methylsulfonic acid)-1H-tetrzol sodium salt, 2-methyl-1H-tetrazol-5ylthio,-5-ylthio, 1,2,3-triazol-5-ylthio, 1-methyl-1,2,3-triazol-5-ylthio, 2-methyl-1,2,3-triazol-5-ylthio, 4-methyl-1,2,3-triazol-5-ylthio, pyrid-2-ylthio N-oxide, 6-methoxy-2-(N-oxide)-pyridaz-3-ylthio, 6-hydroxypyridaz-3-ylthio, 1-methylpyrid-2-ylthio, 1-methylpyrid-4-ylthio, 2-hydroxypyrimid-4-ylthio, 1,4,5,6-tetrahydro-5,6-dioxo-4-methyl-as-triazin-3-ylthio, 1,4,5,6-tetrahydro-4-(2-formylmethyl)-5,6-dioxo-astriazin-3-ylthio, 2,5-dihydro-5-oxo-6-hydroxy-astriazin-3-ylthio, 2,5-dihydro-5-oxo-6-hydroxy-astriazin-3-ylthio sodium salt, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, 2,5-dihydro-5-oxo-6-methoxy-2-methyl-astriazin-3-ylthio, 2,5-dihydro-5-oxo-as-triazin-3-ylthio, 2,5-dihydro-5-oxo-2-methyl-as-triazin-3-ylthio, 2,5-dihydro-5-oxo-2,6-dimethyl-as-triazin-3-ylthio, tetrazole[1,5-b]pyridazin-6-ylthio and 8-aminotetrazolo[1,5-b]pyridazin-6-ylthio; the corresponding sulfoxides and sulfones of the above heterocyclic thio groups, and the like.

Examples of the above group when $R_7$ is other than a heterocyclic group include $C_1$ to $C_6$ alkylthio groups such as methylthio, ethylthio, (sec-butyl)thio, (t-amyl)thio and (n-hexyl)thio, $C_7$ to $C_{12}$ phenylalkylthio groups such as 2-phenylpropylthio, benzylthio, 1-phenyl(n-amyl)thio and 4-phenyl(n-butyl)thio; $C_1$ to $C_6$ substituted alkylthio groups such as cyanomethylthio, 2-hydroxyethylthio, 2-nitropropylthio, 2-carbamoyl(-sec-butyl)thio, 5-chloroamylthio, 4-carboxyamylthio, 6-carbamoyloxyhexylthio, 2-methoxyethylthio, isopropoxy(t-butyl)thio, 2-aminoethylthio, 2,5-dihydroxyamylthio, 3,3-dibromo(n-butyl)thio, 3-chloro-2-iodopropylthio and 4-acetoxy-6-fluorohexylthio; $C_7$ to $C_{12}$ substituted phenylalkylthio groups such as 3-(3,4-diiodophenyl)propylthio, 1-(3-chloro-4-fluorophenyl)ethylthio, 6-(4-cyanophenyl)hexylthio, 3-phenyl-1-chloro(-sec-butyl)thio, 2-phenyl-2-hydroxyethylthio, 5-phenyl-2-hydroxyamylthio, 2-(3-nitrophenyl)-3-ethoxypropylthio, 5,6-dihydroxy-2-(4-ethyl-2-hydroxyphenyl)hexylthio and 5-carbamoyl-3-nitro-2-(2,4-dimethoxyphenyl) amylthio; phenylthio, and (substituted phenyl)thio groups, and the corresponding sulfoxide and sulfone analogs thereof.

Examples of the (substituted phenyl)thio groups represented by $R_7$ include groups such as 4-chlorophenylthio, 2,6-dichlorophenylthio, 2,5-dichlorophenylthio, 3,4-dichlorophenylthio, 3-chlorophenylthio, 3-bromophenylthio, 4-bromophenylthio, 3,4-dibromophenylthio, 3-chloro-4-fluorophenylthio, 2-fluorophenylthio, 4-hydroxyphenylthio, 3-hydroxyphenylthio, 2,4-dihydroxyphenylthio, 3- or 4-nitrophenylthio, 4-cyanophenylthio, 4-methylphenylthio, 2,4-dimethylphenylthio, 2-methylphenylthio, 4-(isopropyl)phenylthio, 4-ethylphenylthio, 3-(n-propyl)phenylthio, 2,6-dimethoxyphenylthio, 4-methoxyphenylthio, 3-ethoxyphenylthio, 4-(iso-propoxy)phenylthio, 4-(t-butoxy)phenylthio, 3-ethoxy-4-methoxyphenylthio, a 3- or 4-(trifluoromethyl)phenylthio, 4-carboxyphenylthio, 2,4-di(protected carboxy)phenylthio, 3-(protected hydroxymethyl)phenylthio, 3,4-di(hydroxymethyl)phenylthio, 2-(aminomethyl)phenylthio, 2,4-di(protected aminomethyl)phenylthio, 3-(N-(methylsulfonylamino))phenylthio, 3-methyl-4-hydroxyphenylthio, 3-chloro-4-hydroxyphenylthio, 2-methoxy-4-bromophenylthio, 4-ethyl-2-hydroxyphenylthio, 3-hydroxy-4-nitrophenylthio, 2-hydroxy-4-chlorophenylthio, and the corresponding sulfoxide and sulfone analogs thereof.

A preferred group of examples of the group

include: 4-(protected carboxymethyl)-5-methyl-1,3-thiazol-2-ylthio, 1,3,4-triazol-5-ylthio, 2-methyl-1,3,4-triazol-5-ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(protected carboxymethyl)-1H-tetrazol-5-ylthio, 1-(methylsulfonic acid)-1H-tetrazol-5-ylthio, 1-(methylsulfonic acid)-1H-tetrazol-5-ylthio sodium salt, 1,2,3-triazol-5-ylthio, 1,4,5,6-tetrahydro-5,6-dioxo-4-methylas-triazin- 3-ylthio, 1,4,5,6-tetrahydro-4-(formylmethyl)-5,6-dioxo-as-triazin-3-ylthio, 2,5-dihydro-5-oxo-6-hydroxy-2-methyl-as-triazin3 -ylthio sodium salt, 2,5-dihydro-5-oxo-6-hydroxy-2-methyl-as-triazin-3-ylthio, tetrazolo[1,5-b]pyridazin-6-ylthio, 8-aminotetrazolo[1,5-b]pyridazin-6-ylthio, methylthio, phenylthio, phenylsulfonyl, methylsulfonyl, methylsulfoxide, and phenylsulfoxide.

In the above Formula I, $R_2$ can be an acyl group of the formula

—COR$_8$

Examples of such a group include when $R_8$ is: hydrogen (the formyl group); $C_1$ to $C_6$ alkyl, such as acetyl, propionyl, sec-butylcarbonyl, t-amylcarbonyl and the like; $C_1$ to $C_6$ substituted alkyl, such as monofluoroacetyl, (3-cyanopropyl)carbonyl, 4,5-dichloroamylcarbonyl, 2-carboxy-1-nitroethylcarbonyl and the like; phenyl (the benzoyl group); substituted phenyl, for example, 4-methoxybenzoyl, 2,4-dimethylbenzoyl, 3-nitrobenzoyl, 4-trifluoromethylbenzoyl, 2,4-di(alkyloxycarbonyl)benzoyl, 2-(aminomethyl)benzoyl, 3-hydroxy-4-nitrobenzoyl, and the like; $C_7$ to $C_{12}$ arylalkyl, such phenylmethylcarbonyl, 2-phenylethylcarbonyl, phenyl(t-butyl)carbonyl, 3-phenylamylcarbonyl and the like; $C_7$ to $C_{12}$ substituted arylalkyl, such as 3-(3,4-diiodophenyl)propylcarbonyl, 1-(3-chloro-4-fluorophenyl)ethylcarbonyl, 6-(4-cyanophenyl) hexylcarbonyl, 3-phenyl-1-chloro(secbutyl)carbonyl, 2-phenyl-2-hydroxyethylcarbonyl, 5-pheny- 2-hydroxyamylcarbonyl, 2-(3-nitrophenyl)-3-ethoxypropylcarbonyl, 5,6-dihydroxy-2-(4-ethyl-2-hydroxyphenyl)hexylcarbonyl, 5-carbamoyl-3-nitro-2-(2,4-dimethoxyphenyl)amylcarbonyl and the like; perfluoro $C_2$ to $C_4$ alkyl, such as perfluoropropionyl, perfluorobutyryl, perfluoropentanoyl, and the like; amino (the primary amido group); (monosubstituted)amino, such as N-methylamido, N-ethylamido, N-(iso-propyl)amido, N-(n-hexyl)amido, N-phenylamido, N-(4-chlorophenyl)amido, N-(2-hydroxy-4-bromophenyl)amido, N-benzylamido, N-(2-phenyl(n-propyl))amido, and the like; and (disubstituted)amino, such as N,N-dimethylamido, N,N-methylphenylamido, N,N-(phenyl)(phenethyl)amido, N,N-ethyl(4-cyanophenyl)amido, N,N-dibenzylamido, N,N-methylethylamido, N,N-methylbenzylamido, and the like.

A preferred group of examples of the acyl group formed with $R_8$ is the acetyl, monofluoroacetyl, and propionyl.

When $R_2$ in the above Formula I is a carboxyl group of the formula

—COOR$_9$ examples include groups when $R_9$ is: $C_1$ to $C_6$ alkyl, such as ethoxycarbonyl, n-propoxycarbonyl, sec-butoxycarbonyl, t-amloxycarbonyl and the like; $C_1$ to $C_6$ substituted alkyl, such as (3-cyanopropyloxy)carbonyl, 4,5-dichloroamyloxycarbonyl, 2-carboxy-1-nitroethoxycarbonyl, and the like; phenyl (the phenoxycarbonyl group), substituted phenyl, for example, 4-methoxyphenoxycarbonyl, 2,4-dimethylphenoxycarbonyl, 3-nitrophenoxycarbonyl, 4-trifluoromethylphenoxycarbonyl, 2,4-di(methoxycarbonyl)phenoxycarbonyl, 2-(aminomethyl)phenoxycarbonyl, 3-hydroxy-4-nitrophenoxycarbonyl, and the like; $C_7$ to $C_{12}$ arylalkyl, such benzyloxycarbonyl, 2-phenylethoxycarbonyl, phenyl(t-butoxy)carbonyl, 3-phenylamyloxycarbonyl and the like; trihalomethyl, such as trifluoromethoxycarbonyl, trichloromethoxycarbonyl, tribromomethoxycarbonyl or triiodomethoxycarbonyl; or $C_7$ to $C_{12}$ substituted arylalkyl, such as 3-(3,4-diiodophenyl)propoxycarbonyl, 1-(3-chloro-4-fluorophenyl)ethoxycarbonyl, 6-(4-cyanophenyl)hexyl oxycarbonyl, 3-phenyl-1-chloro(-sec-butoxy)carbonyl, 2-phenyl-2-hydroxyethoxycarbonyl, 5-phenyl-2-hydroxyamyloxycarbonyl, 2-(3-nitrophenyl)-3-ethoxypropoxycarbonyl, 5,6-dihydroxy-2-(4-ethyl-2-hydroxyphenyl)hexyloxycarbonyl, and 5-carbamoyl-3-nitro-(2,4-dimethoxyphenyl)amyloxycarbonyl, and the like.

Further examples of the above—COOR$_9$ group are when $R_9$ is: a carboxy-protecting group, such as allyl carboxylate, p-methoxybenzyl carboxylate, di-(4-methoxy) benzhydryl carboxylate, benzhydryl carboxylate, 2,2,2-trichloroethyl carboxylate, trimethylsilyl carboxylate, (t-butyl)dimethylsilyl carboxylate, β-(trimethylsilyl)ethyl carboxylate, trityl carboxylate, 4,4', 4"-trimethoxytrityl carboxylate, p-toluenesulfonylethyl carboxylate, and the like; a non-toxic, metabolically-labile ester-forming group, such as methoxymethyl carboxylate, 5-methyl-2-oxo-1,3-dioxolen-4-ylmethyl carboxylate, ethylthiomethyl carboxylate, pivaloyloxymethyl carboxylate, 3-phthalidyl carboxylate, 1-(ethoxycarbonyloxy) ethyl carboxylate, 1-(methylaminocarbonyloxy)ethyl carboxylate, and the like.

A preferred group of examples of the carboxy group—COOR$_9$ is when $R_9$ is a $C_1$ to $C_6$ alkyl group or a carboxy-protecting group. An especially preferred group of examples of the above carboxy group is when $R_9$ is methyl, ethyl, n-propyl, benzyl, allyl, t-butyl, or 4-nitrobenzyl.

Examples of the group—COOR$_{11}$ are given above in conjunction with the carboxy group—COOR$_9$.

A preferred group of examples of the group—COOR$_{11}$ occurs when $R_{11}$ is a $C_1$ to $C_6$ alkyl group. An especially preferred carboxyl group of the above formula is ethyl carboxylate.

Examples of the phosphonato group

—PO$_3$(R$_{10}$)$_2$ includes groups wherein each $R_{10}$ is a $C_1$ to $C_6$ alkyl group, such as dimethylphosphonato, diethylphosphonato, methylethylphosphonato, methyl(iso-propyl)phosphonato, amylhexylphosphonato, dihexylphosphonato and the like; groups wherein each $R_{10}$ is a $C_1$ to $C_6$ substituted alkyl group, such as di(2-nitroethyl)phosphonato, (4-chlorobutyl)(2-carboxyethyl)phosphonato, (3-aminoamyl)(aminomethyl)phosphonato, (2-hydroxyethyl)(2-carbamoylethyl)phosphonato, (3-carbamoyloxypropyl)(2-carbamoyloxypropyl)phosphonato, (3-chlorobutyl)(2-bromobutyl)phosphonato and like groups; groups when $R_{10}$ is phenyl, (the diphenylphosphonato group); groups wherein each $R_{10}$ group is substituted phenyl, for example, di(4-methoxyphenyl)phosphonato, (4-methoxyphenyl)(2-methoxyphenyl)phosphonato, (3-cyanophenyl)(3-nitrophenyl)phosphonato, (3-chlorophenyl)(2,4-dimethylphenyl)phosphonato, (3-aminophenyl)(2,4-diaminophenyl)phosphonato, di(2,4-dimethoxyphenyl)phosphonato, (2,4-methylphenyl)(2,4-methoxyphenyl)phosphonato, (3,5-dinitrophenyl)(2,4-aminophenyl)phosphonato, and the like; groups wherein each $R_{10}$ is a $C_7$ to $C_{12}$ arylalkyl radical, such as di(benzyl)phosphonato, di(2-phenylethyl)phosphonato, benzyl(2-phenylethyl)phosphonato, 3-phenylhexyl(phenyl t-butyl)phosphonato, and the like; groups wherein each $R_{10}$ is a $C_7$ to $C_{12}$ substituted arylalkyl radical, such as di(4-methoxyphenylmethyl)phosphonato, di(3-phenyl-2-hydroxypropyl)phosphonato, di(3-(4-methylphenyl)-4-aminobutyl)phosphonato, (5-(4-cyanophenyl)amyl)(2-phenyl-2-carbamoylethyl)phosphonato, (2-(3,5-dinitrophenyl)ethyl)(2-(4-hydroxyphenyl)ethyl)phosphonato, (4-phenyl-3-aminobutyl)(4-phenyl-2-iodobutyl)phosphonato, and like groups.

Furthermore, each of the $R_{10}$ variables of the above phosphonato group can be chosen from different groups of substituents. For example, one $R_{10}$ can be a $C_1$ to $C_6$ alkyl group while the other $R_{10}$ is $C_1$ to $C_6$ substituted alkyl, phenyl, substituted phenyl, $C_7$ to $C_{12}$ arylalkyl or a $C_7$ to $C_{12}$ substituted arylalkyl group. Similarly, when one $R_{10}$ is a $C_1$ to $C_6$ substituted alkyl substituent group, the other $R_{10}$ can be $C_1$ to $C_6$ alkyl, phenyl, substituted phenyl, $C_7$ to $C_{12}$ arylalkyl or a $C_7$ to $C_{12}$ substituted arylalkyl group.

A preferred group of phosphonato groups are the dimethylphosphonato, diethylphosphonato, and diphenylphosphonato groups.

A preferred group of the compounds of Formula I are when $R_3$ and $R_4$ are each hydrogen, and are referred to as the "unsubstituted vinyl phosphonate adducts". Preferred unsubstituted vinyl phosphonate adducts are when either $R_5$ or $R_6$ is hydrogen and the other is an amino-protecting group.

The preferred unsubstituted vinyl phosphonate adducts contain four preferred groups which are distinguished by the substituent at $R_2$. These four preferred groups occur when $R_2$ is:

(a) —COOR$_9$(the "carboxy vinyl phosphonate adducts");

(b) 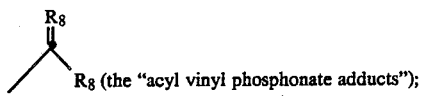 R$_8$ (the "acyl vinyl phosphonate adducts");

(c) —CN(the "cyano vinyl phosphonate adducts"); and (d) 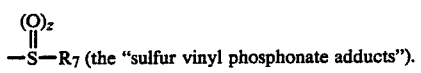 —S—R$_7$ (the "sulfur vinyl phosphonate adducts").

A preferred group of carboxy vinyl phosphonate adducts sets $R_9$ as methyl, ethyl, n-propyl, or benzyl. More preferred carboxy vinyl phosphonate adducts are those wherein either $R_5$ or $R_6$ is hydrogen and the other is a t-butoxycarbonyl group, and $R_{1a}$ and $R_{1b}$ are the same and are either methyl or ethyl.

A preferred group of acyl vinyl phosphonate adducts are compounds wherein $R_8$ is ethyl or monofluoroacetyl. A more preferred group sets either $R_5$ or $R_6$ as hydrogen and the other as a t-butoxycarbonyl group, and sets $R_{1a}$ and $R_{1b}$ as methyl.

A preferred group of cyano vinyl phosphonate adducts are compounds wherein either $R_5$ or $R_6$ is hydrogen and the other is a t-butoxycarbonyl group, and $R_{1a}$ and $R_{1b}$ are ethyl.

Finally, a preferred group of sulfur vinyl phosphonate adducts are wherein Z is two and $R_7$ is methyl (i.e., the methylsulfonyl vinyl phosphonate adducts). Preferred methylsulfonyl compounds are when either $R_5$ or $R_6$ is hydrogen and the other is a t-butoxycarbonyl group, and $R_{1a}$ and $R_{1b}$ are each methyl.

Above all, a preferred group of the compounds of Formula I are the 4-(S) vinyl phosphonate adducts of the formula

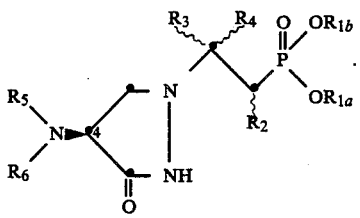

Preferred 4-(S) compounds occur when $R_3$ and $R_4$ are hydrogen, and especially when either $R_5$ or $R_6$ is hydrogen and the other is an amino-protecting group.

A preferred group of the preferred 4-(S) compounds occur when $R_2$ is cyano. Preferred 4-(S) cyano vinyl phosphonate adducts set either $R_5$ or $R_6$ as hydrogen and the other as a t-butoxycarbonyl group, and set $R_{1a}$ and $R_{1b}$ as ethyl.

II. SYNTHESIS OF THE COMPOUNDS OF FORMULA I AND THE REQUISITE STARTING MATERIALS

The vinyl phosphonate adducts of Formula I are prepared by the general reaction set forth below in Scheme 1.

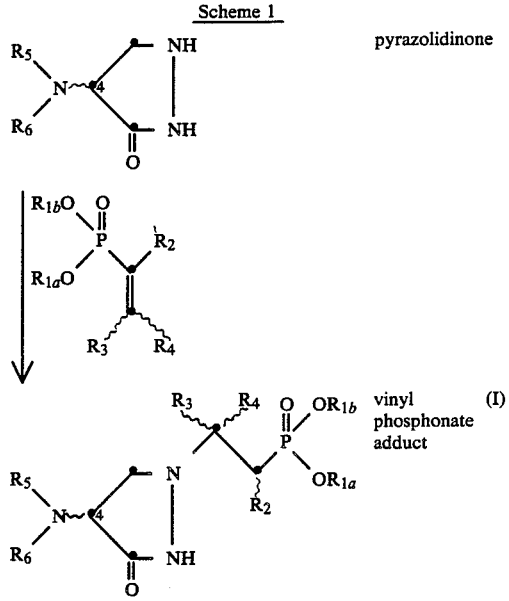

In the above Scheme 1, $R_{1a}$, $R_{1b}$, $R_2$, $R_3$, and $R_4$, are the same as for Formula I. $R_5$ and $R_6$ are the same as Formula I except that they are not simultaneously hydrogen. Furthermore, it is preferred that any amino, hydroxy or carboxy substituents at $R_2$, $R_3$ and $R_4$ be in the protected form.

The stereospecificity at $C_4$ of the vinyl phosphonate adduct (Formula I) of the above reaction is determined by the $C_4$ stereochemistry of the pyrazolidinone starting material. Thus, a 4-(S) pyrazolidinone starting material will yield a 4-(S) vinyl phosphonate adduct (Formula I). Furthermore, the stereospecificity of the reaction for the substituents $R_2$, $R_3$, and $R_4$ is unpredictable with a mixture of stereoisomers concerning these substituents as likely products of the reaction.

The alkylation of the $C_1$-nitrogen of the pyrazolidinone ring with a vinyl phosphonate reagent is initiated by combining a 1:1 molar ratio of the two reactants, although an excess of either reactant permissable. The solvent for the alkylation is an alcoholic solvent such as methanol, ethanol or isopropanol. Methanol is the preferred solvent.

The alkylation is usually carried out from between about 0° C. to about room temperature. The reaction is a very rapid one, requiring as little as 1 hour but occassionally up to 48 hours for completion.

The progress of the alkylation is monitored by conventional chromatographic techniques (such as thin layer chromatography or analytical-scale high pressure liquid chromatography) or spectroscopic techniques (such as infrared spectrometry or nuclear magnetic resonance spectroscopy). Spectroscopic and chromatographic techniques may also be combined to monitor the progress of the reaction. When the monitoring technique(s) demonstrates that the reaction is substantially complete, the product from the above reaction is isolated by conventional methods. The vinyl phosphonate adducts of Formula I are intermediates to bicyclic pyrazolidinone antimicrobials. The synthetic route to the antimicrobials is represented below in Scheme 2.

Scheme 2

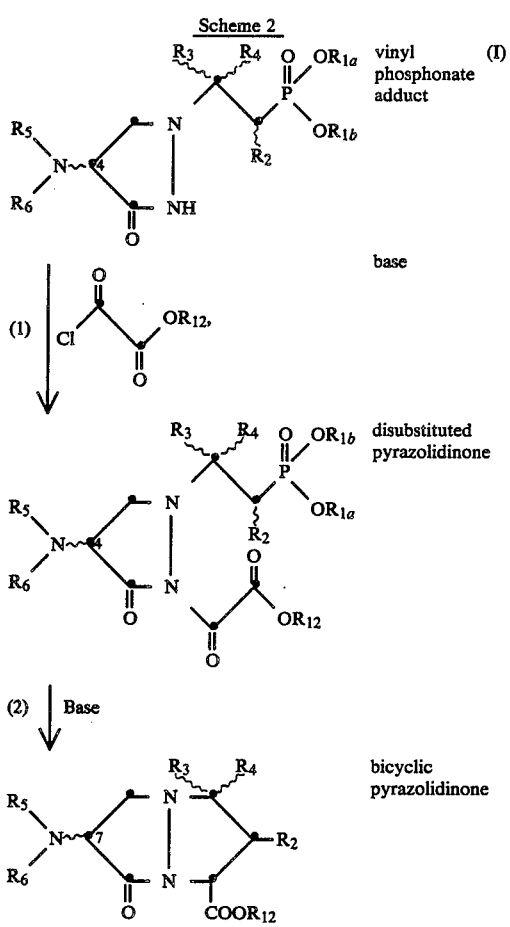

In the above Scheme 2, $R_1{}^a$, $R_1{}^b$, $R_2$, $R_3$, $R_4$, $R_5$ and $R_6$ are as defined for Scheme 1. $R_{12}$ is a carboxyprotecting group or a non-toxic, metabolically-labile, ester-forming group. In addition, the stereospecificity at $C_7$ of the bicyclic pyrazolidinone in the synthetic route of Scheme 2 is determined by the stereochemistry at $C_4$ of the vinyl phosphonate adduct. Thus, a 4-(S) vinyl phosphonate adduct will yield a 7-(S) bicyclic pyrazolidinone product.

The vinyl phosphonate adduct obtained from the alkylation reaction (Scheme 1) is acylated at the 2-position nitrogen with an oxalate ester acid chloride (after deprotonation of the pyrazolidinone with di(isopropyl)ethylamine). The acylation reaction yields the corresponding 1,2-disubstituted pyrazolidinone.

In the acylation reaction approximately one molar equivalent of the amine base and one molar equivalent or less of the oxalate reactant per equivalent of the adduct reactant are combined. The three reactants can be combined in any order. The usual order is to combine the adduct and the oxalate reactants then add the amine base.

The vinyl phosphonate adduct may be acylated in either chlorinated hydrocarbon or ether solvents. Methylene chloride is the preferred solvent.

The acylation reaction is often complete in as little as one hour. However, the reaction may need to be stirred at the appropriate temperature for as long as approximately 12 hours to reach completion.

At the time when the three reactants are being combined, the temperature of the acylation mixture should be maintained from approximately −78° C. to approximately −50° C. The reaction mixture is often stirred for approximately 1 hour at this temperature then allowed to warm to room temperature with stirring.

The 1,2-disubstituted pyrazolidinone obtained from Reaction 1 is then cyclized to give the bicyclic pyrazolidinone, as depicted in Reaction 2.

In the cyclization reaction an equimolar or greater amount of the sodium hydride base per equivalent of the pyrazolidinone reactant is used. Ethers, and in particular tetrahydrofuran, are the preferred solvents. The reactants are usually combined and stirred at approximately 0° C. for approximately 15 minutes to approximately 1 hour. The reaction mixture can be stirred at room temperature for as long as 24 hours.

A preferred reaction sequence for the above Scheme 2 is to acylate the vinyl phosphonate adduct and then cyclize the product without isolating the 1,2-disubstituted pyrazolidinone. In this preferred combination reaction, the vinyl phosphonate adduct and the acylating reagent are combined in any order and in the stoichiometry discussed for the acylation reaction. The solvent for the combination reaction is the same as for the acylation alone, including the preference for methylene chloride. The combination reaction requires more equivalents of di(isopropyl)ethylamine base per equivalent of adduct starting material (at least 2 versus at least 1) to effect both the acylation and the subsequent cyclization. The combination reaction mixture is stirred for from approximately 15 minutes to approximately 18 hours from about 0° C. to about room temperature.

The progress of Reactions 1 and 2 in Scheme 2 is monitored by conventional chromatographic techniques (such as thin layer chromatography or analytical-scale high pressure liquid chromatography) or spectroscopic techniques (such as infrared spectrometry or nuclear magnetic resonance spectroscopy). Spectroscopic and chromatographic techniques may also be combined to monitor the progress of the reactions. When the monitoring technique(s) demonstrates that the reaction(s) are substantially complete, the products from the above reactions are isolated by conventional methods.

The bicyclic pyrazolidinone compounds produced by the reactions in Scheme 2 above are 7-(protected amino) intermediate compounds (i.e., when either $R_5$ or $R_6$ is an amino-protecting group and the other is hydrogen). Replacing the amino-protecting group of the 7-(protected amino) compounds with an acyl group derived from a $C_1$ to $C_{30}$ carboxylic acid converts them to the antimicrobial bicyclic pyrazolidinone compounds. The acyl groups employed are typically those used to achieve the same purpose when bonded to the 6-amino group of a penicillin or a 7-amino group of a cephalosporin.

The first step for the acylation of a 7-(protected amino) bicyclic pyrazolidinone compound ("7-protected amino nucleus") is the removal of the amino-protecting group. For example, the trimethylsilyl protecting group is removed by simple hydrolysis, the t-butoxycarbonyl group is removed by either acidic hydrolysis (with trifluoroacetic acid) or acidolysis (hydrochloric acid in glacial acetic acid), and the allyloxycarbonyl group is removed as a palladium complex. The conditions for the removal of other groups are well known in the cephalosporin and penicillin arts.

Removal of the acid-labile amino-protecting groups usually yields the 7-amino nucleus as a salt. The salt of the nucleus is neutralized by conventional procedures before acylation. For instance, the removal of the t-butoxycarbonyl group with trifluoroacetic acid leaves the trifluoroacetate salt of the resultant 7-amino nucleus. The salt is taken up in tetrahydrofuran and bis(-trimethylsilyl)trifluoroacetamide is added to yield the corresponding (neutralized) 7-amino compound. The neutralized compound can either be isolated then acylated or acylated in situ.

The methods for the acylation of the neutralized 7-amino bicyclic pyrazolidinone with the acyl side chain are similar to the methods for the acylation of 6-aminopenicillanic acid, 7-aminodesacetoxycephalosporanic acid and 7-aminocephalosporanic acid. One method is to simply combine the 7-amino nucleus with an acid chloride or acid bromide in the presence of an acid scavenger. The acid chloride or acid bromide may be formed in situ. Another method is to combine the 7-amino nucleus with the free carboxylic acid form of the side chain (or its acid salt) and a condensing agent. Suitable condensing agents include N,N'-disubstituted carbodiimides such as N,N'-dicyclohexylcarbodiimide, N,N'-diethylcarbodiimide, N,N'-di-(n-propyl)carbodiimide, N,N'-di-(iso-propyl)carbodiimide, N,N'-diallylcarbodiimide, N,N'-bis(p-dimethylaminophenyl)carbodiimide, N-ethyl-N'-(4''-ethylmorpholinyl)carbodiimide and the like. Other suitable carbodiimides are disclosed by Sheehan in U.S. Pat. No. 2,938,892 and by Hofmann et al. in U.S. Pat. No. 3,065,224. Azolides, such as N,N'-carbonyldiimidazole and N,N'-thionyldiimidazol, may also be used as condensing agents. Dehydrating agents such as phosphorus oxychloride, the alkoxyacetylenes and 2-halogenopyridinium salts (such as 2-chloropyridinium methyl iodide, 2-fluoropyridinium methyl iodide, and the like) may be used to couple the free acid or its acid salt with the 7-amino nucleus.

Another acylation method entails first converting the free carboxylic acid form (or the corresponding salt) of the acyl side chain to the active ester derivative which is in turn used to acylate the nucleus. The active ester derivative is formed by esterifying the free acid form with groups such as p-nitrophenol, 2,4-dinitrophenol, trichlorophenol, pentachlorophenol, 2-chloro-4,6-dimethoxytriazene, N-chlorosuccinimide, N-chloro maleic imide, N-chlorophthalimide, 1-hydroxy-1H-benzotriazole or 1-hydroxy6-chloro-1H-benzotriazole. The active ester derivatives can also be mixed anhydrides, which are formed with groups such as methoxycarbonyl, ethoxycarbonyl, isobutoxycarbonyl, trichloromethylcarbonyl and iso-but-2-ylcarbonyl and the carboxylic acid of the acyl side chain. The mixed anhydrides are synthesized by acylating the carboxylic acid of the acyl side chain.

Alternatively, the 7-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (such as tetrahydrofuran, acetonitrile, and the like). The resultant EEDQ derivative is used in situ to acylate the 7-amino nucleus.

The antimicrobial activity of the bicyclic pyrazolidinones acylated with the appropriate acyl group derived from a $C_1$ to $C_{30}$ carboxylic acid is further enhanced on removal of any remaining amino, hydroxy and/or carboxy protecting groups on the molecule. As discussed above, such removal methods are generally well known in the cephalosporin, penicillin and, peptide arts. Once the carboxy groups are deprotected, the non-toxic, metabolically-labile, ester-forming ("oral ester") group(s) may be put in place on the desired carboxy groups at $R_{12}$, $R_2$, $R_3$ and $R_4$. The methods for making the oral ester derivatives are well known in the cephalosporin and penicillin arts.

The bicyclic pyrazolidinone antimicrobial compounds and the corresponding intermediates are disclosed in C. J. Barnett, R. E. Holmes, L. N. Jungheim, S. K. Sigmund, and R. J. Ternansky, U.S. patent application Ser. No., 862,906, filed this even date, herein incorporated by reference, which application in turn is a continuation-in-part of L. N. Jungheim and S. K. Sigmund, U.S. patent application No. 729,021, filed Apr. 30, 1985, now abandoned, herein incorporated by reference.

A $C_4$-racemic mixture of pyrazolidinone starting materials for the reaction in Scheme 1 are synthesized according to the process depicted below in Scheme 3.

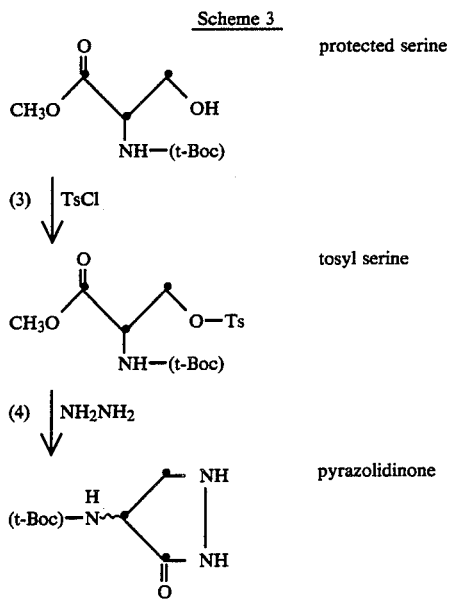

The above Scheme depicts the synthesis of 4-(t-butoxycarbonylamino) pyrazolidinone starting materials. Pyrazolidinone starting materials with different amino-protecting groups are obtained by starting with a different protecting group on the protected serine derivative.

The first step in the synthesis of the pyrazolidinone starting materials, represented by Reaction 3 in the above Scheme, is the tosylation of the hydroxy group of the protected serine derivative. The tosylation is carried out in methylene chloride with p-toluenesulfonyl chloride in the presence of a catalytic amount of 4-dimethylaminopyridine and greater than one equivalent of pyridine. The reaction mixture is stirred at room temperature overnight.

The tosylated serine obtained is cyclized to give the pyrazolidinone. The cyclization represented by Reaction 4 is carried out by adding the tosyl serine to a solution of 97% hydrazine in methylene chloride under nitrogen. The mixture is then stirred at room temperature for five hours.

The stereospecific synthesis of the chiral pyrazolidinone starting materials is diagramed below in Scheme 4.

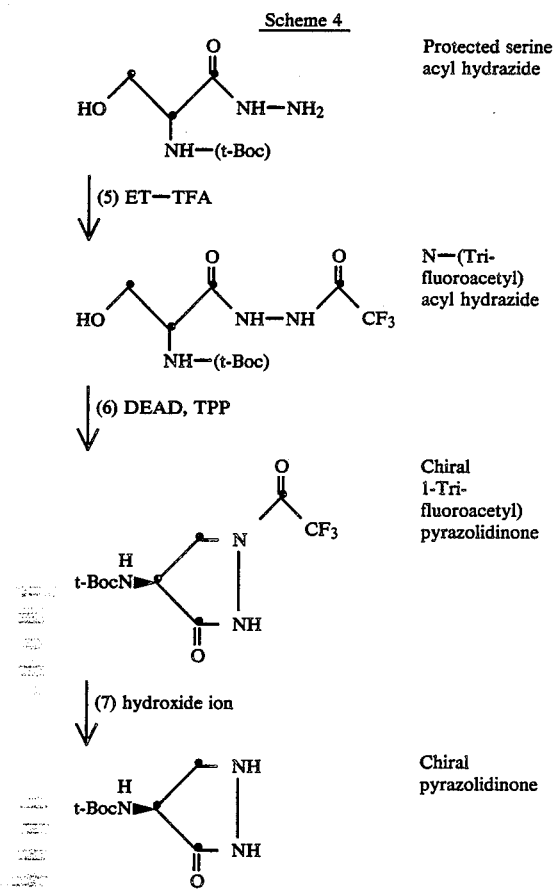

The above Scheme depicts the synthesis of chiral 4-(S)-(t-butoxycarbonylamino) pyrazolidinone compounds. Pyrazolidinone compounds with the 4-(R) configuration are synthesized by starting with the protected D-serine acyl hydrazide instead of the L-isomer depicted above. Both 4-(R) or 4-(S) compounds with amino-protecting groups other than t-butoxy carbonyl are synthesized from the corresponding serine enantiomer substituted with an amino-protecting group other than t-butoxycarbonyl.

The protected serine acyl hydrazide precursor of Scheme 4 is synthesized in a procedure analogous to B. Iselin and R. Schwyzer, *Helv. Chim. Acta*, 44, p. 169 (1961). The precursor is then acylated with the trifluoroacetyl moiety, as set forth in Reaction 5 in the Scheme. The hydrazide precursor is acylated with an excess of ethylthio trifluorothioacetate ("ET-TFA") in ethanol. The reaction mixture is stirred at room temperature for 65 hours.

The N-(trifluoroacetyl) acyl hydrazide obtained from Reaction 5 is cyclized with triphenylphosphine ("TPP") and diethyl azodicarboxylate ("DEAD"), as depicted above in Reaction 6.

The stoichiometry of the cyclization of Reaction 6 has the N-(trifluoroacetyl) acyl hydrazide, phosphine, and diethyl azodicarboxylate reagents present in at least approximately a 1:1:1 molar ratio. The reaction will proceed in the presence of molar excesses above this ratio of any of the reactants.

The cyclization is initiated by first combining (in any order) the solvent, the N-(trifluoroacetyl) acyl hydrazide, and the phosphine, and secondly adding the azodicarboxylate reagent.

The temperature of Reaction 6 is not a critical parameter. The cyclization can be carried out at a temperature from approximately the freezing point to approximately the reflux temperature of the solvent. The preferred temperature is approximately room temperature.

The duration of Reaction 6 can be from approximately five minutes to approximately twenty four hours. The progress of the cyclization can be monitored by standard methods (such as thin layer chromatography, high performance liquid chromatography, etc.) The process is stopped when the monitoring method demonstrates that the reaction is substantially complete.

The solvents for the cyclization are aromatic hydrocarbon solvents such as benzene, toluene or xylenes; ethers such as diethyl ether, tetrahydrofuran, or 1,4-dioxane; chlorinated hydrocarbons such as methylene chloride, chloroform, carbon tetrachloride, dichloroethane, or chlorobenzene; amides such as dimethylformamide and dimethylacetamide; and other solvents such as hexamethylphosphoramide. Tetrahydrofuran is the preferred solvent. It is also desirable, but not essential, to dry and deoxygenate the solvent before use in the process.

While Reaction 6 in the above Scheme depicts the use of diethyl azodicarboxylate, the dimethyl and di(isopropyl)azodicarboxylate analogs can also be used in the reaction.

The chiral 1-(trifluoroacetyl)pyrazolidine obtained from Reaction 6 is deacylated with dilute sodium hydroxide solution. The deacylation is represented as Reaction 7 in the Scheme. The deacylation entails generally suspending the chiral 1-(trifluoroacetyl)pyrazolidine in water and adding at least two equivalents of a dilute aqueous solution of either sodium hydroxide or potassium hydroxide. For instance, a two-fold excess of 1M sodium hydroxide solution can be used. It is preferred to have the initial pH of the solution from between about 11 to about 12. The resultant solution can be stirred from about 10 minutes to about 3 hours at a temperature from about 10° C. to about 25° C. When the reaction is substantially complete the reaction solution is neutralized by the addition of dilute acid, such as 1N hydrochloric acid.

The optimal reaction time for the deacylation can be determined by monitoring the progress of the reaction with conventional chromatographic methods (such as thin layer chromatography, high performance liquid chromatography, or column chromatography), or spectroscopic methods, (such as infrared spectroscopy, nuclear magnetic resonance spectrometry or mass spectrometry) or a combination of both methods. A preferred reaction time is from between about 30 minutes to about 1.5 hours.

The synthesis of the above pyrazolidinone starting materials is further described by L. N. Jungheim and R. E. Holmes , U.S. patent application Ser. No. 862,917, filed this even date, herein incorporated by reference, which application is in turn a continuation-in-part of L. N. Jungheim, U.S. patent application Ser. No. 728,734, filed Apr. 30, 1985,now abandoned, herein incorporated by reference.

The vinyl phosphonate starting materials in Scheme 1 are made by methods known in the art and/or are commercially available. The synthesis of some of these starting materials are also described in the Experimental Section below.

III. DESCRIPTION OF THE ANTIMICROBIAL PROPERTIES OF THE 7-SUBSTITUTED BICYCLIC PYRAZHOLIDINONES

The compounds of Formula I are intermediates to the bicyclic pyrazolidinones (depicted in Scheme 2). The bicyclic pyrazolidinone antimicrobial compounds inhibit the growth of certain organisms pathogenic to man and animals. The preferred bicyclic pyrazolidinone antimicrobial compounds are compounds wherein the various amino, hydroxy and/or carboxy-protecting groups have been removed and either $R_5$ or $R_6$ is an acyl group derived from a $C_1$ to $C_{30}$ carboxylic acid and the other is hydrogen. The antimicrobial activity can be demonstrated in vitro using standard tube-dilution techniques. These in vitro tests demonstrate that, in general, the 7-(S) isomers have better antimicrobial activity than either the corresponding 7-(R) isomers or a mixture of the two isomers. Representative pathogens which are sensitive to the antimicrobial compounds include *Staphylococcus aureus* X.1, *Streptococcus pyogenes* C203, *Streptococcus pneumoniae* Park, *Hemophilus influenzae* 76 (ampicillin resistant), *Escherichia coli* N10, *Escherichia coli* EC14, *Escherichia coli* TEM ($\beta$-lactamase producer), *Klebsiella pneumoniae* X26, *Klebsiella pneumoniae* KAE ($\beta$-lactamase producer), *Klebsiella pneumoniae* X68, *Enterobacter aerogenes* C32, *Enterobacter aerogenes* EB17, *Enterobacter cloacae* EB5 (non-$\beta$-lactamase producer), *Salmonella typhi* X514, *Salmonella typhi* B35, *Serratia marcescens* X99, *Serratia marcescens* SE3, *Proteus morganii* PR15, *Proteus inconstans* PR33, *Proteus rettgeri* C24, *Citrobacter freundii* CF17, and the like.

The bicyclic pyrazolidinone antimicrobial compounds that the compounds of this invention are intermediates to are useful for the therapeutic or prophylactic treatment of infections in warm-blooded animals caused by gram-positive, gram-negative, and acid-fast bacteria.

The antimicrobial compounds can be administered orally, parenterally (e.g. intravenously, intramuscularly or subcutaneously) or as a topical ointment or solution in treating bacterial infections of warm-blooded animals.

The bicyclic pyrazolidinone compounds can be formulated into pharmaceutical compositions. In particular, these pharmaceutical compositions are useful for the control of gram-positive and gram-negative bacterial infections and comprise a suitable vehicle and a therapeutically effective amount of the bicyclic pyrazolidinone antimicrobial compounds.

With regard to compositions for oral administration (such as tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as croscarmellose sodium, microcrystalline cellulose, corn starch, sodium starch glycolate, alginic acid and mutable wetting agents such as sodium lauryl sulfate; and lubricants such as magnesium stearate and other metallic stearates, stearic acid, silicone fluid, talc, waxes oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

The pharmaceutical compositions may also be in the form of oral liquid preparations, which may be either (a) aqueous or oily suspensions, solutions, emulsions or syrups; or (b) a dry powder to be reconstituted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol or ethyl alcohol; and preservatives such as methyl or propyl p-hydroxybenzoates or sorbic acid.

The pharmaceutical composition can also be for intravenous (IV) use. Specifically, a water soluble form of the antimicrobial compound can be dissolved in one of the commonly used intravenous fluids and administered by infusion. When used in conjunction with compositions for IV use, the term "suitable vehicle" means such fluids as physiological saline, Ringer's solution or 5% dextrose solution.

For intramuscular preparations a sterile formulation of a suitable salt form of the antimicrobial compound (for example, the hydrochloride salt or sodium salt) can be formulated with a "suitable vehicle". Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

Veterinary pharmaceutical compositions of the antimicrobial compounds may be administered in the feed or the drinking water of farm animals. Alternatively, the compounds can be formulated as intramammary preparations with "suitable vehicles" such as long- or quick-release bases.

The bicyclic pyrazolidinone antimicrobial compounds can also be formulated in unit dosage form in sterile vials, sterile plastic pouches containing a port with a septum, or sterile, hermetically sealed ampoules. The antimicrobial compound (or the corresponding pharmaceutically-acceptable salt) may be a dry powder or in crystalline or lyophylized form. The amount of the antimicrobial compound per unit dosage may vary from about 250 milligrams to about 10 grams.

A "therapeutically effective amount" of the bicyclic pyrazolidinone antimicrobial compounds is from approximately 2.5 mg to about 50 mg of compound per kilogram of body weight. This amount generally totals from about 1 gram to about 12 grams per day for an adult human.

The bicyclic pyrazolidinone antimicrobial compounds can be used to treat or control infectious diseases caused by gram-positive and gram-negative organisms in warm-blooded animals. This method comprises administering to the infected host a therapeutically effective amount of the bicyclic pyrazolidinone antimicrobial compounds. A typical daily dose for an adult human in this method is from about 0.5 grams to about 12 grams.

In practicing this method, the antimicrobial compound can be administered in a single daily dose or in multiple doses per day. The treatment regime may require administration over extended periods of time, for example, for several days or for from two to three weeks. The amount administered per dose or the total amount administered will depend on such factors as the nature and severity of the infection, the age and general health of the patient, and the tolerance to the bicyclic pyrazolidinone antimicrobial compounds of both the patient and the microorganism or microorganisms involved in the infection.

The following Examples are provided to further illustrate the invention. It is not intended that the invention be limited in scope by reason of any of the following Preparations or Examples.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated m.p., n.m.r., m.s., f.d.m.s., f.a.b.m.s., i.r., u.v., anal., HPLC, and TLC, respectively. In addition, the adsorption maxima listed for the i.r. spectra are only those of interest and not all of the maxima observed.

The abbreviations THF and DMF stand for tetrahydrofuran and dimethylformamide, respectively.

In conjunction with the n.m.r. spectra, the following abbreviations are used: "s" is singlet, "d" is doublet, "dd" is doublet of doublets, "t" is triplet, "q" is quartet, "m" is multiplet, and "br.s", "br.d" and "br.t" are broad singlet, doublet and triplet, respectively. "J" indicates the coupling constant in Hertz. "DMSO-$d_6$" is dimethyl sulfoxide where all protons have been replaced with deuterium.

The n.m.r. spectra were obtained on a Varian Associates EM-390 90 MHz, on a Jeol FX-90Q 90 MHz instrument, on a Brüker Corp. 270 MHz instrument or on a General Electric QE-300 300 MHz instrument. The chemical shifts are expressed in δ values (parts per million downfield from tetramethylsilane). The field desorption mass spectra were taken on a Varian-MAT 731 Spectrometer using carbon dendrite emitters. Election Impact Mass Spectra were obtained on a CEC 21-110 instrument from Consolidated Electrodynamics Corporation. Infrared spectra were obtained on a Perkin-Elmer 281 instrument. Ultraviolet Spectra were obtained on a Cary 118 instrument. Specific rotations were obtained on a Perkin-Elmer Q-41 instrument. Thin layer chromatography was carried out on E. Merck silica gel plates. Melting points are uncorrected.

EXPERIMENTAL SECTION

Preparation 1

Methyl 3-(p-Toluenesulfonate)-2-(S)-(t-Butoxycarbonylamino)-Propionate

Methyl (3-hydroxy)-2-(S)-(t-butoxycarbonylamino)-propionate (58 g, 196 mmol), dry methylene chloride (150 ml), p-toluenesulfonyl chloride (43.35 g, 227.4 mmol), 4-(dimethylamino)pyridine (2.4 g, 19.6 mmol) and pyridine (30 ml, 371 mmol) were combined and stirred at room temperature overnight. The reaction solution was concentrated in vacuo to a pale yellow oil. The oil was stored in vacuo overnight, then the white solid that formed was isolated to give 75.33 g of crude product. The product was triturated in petroleum ether (approximately 200 ml) to yield methyl 3-(p-toluenesulfonate)-2-(S)-(t-butoxycarbonylamino)propionate:

n.m.r.: (CDCl$_3$, 90 MHz): δ 7.72, 7.31 (2x dd, 4, aromatic protons), 5.26 (m, 1, nitrogen proton), 4.48 (m, 1, C-2 proton), 4.32 (m, 2, C-3 protons), 3.68 (s, 3, methyl protons of methyl ester), 2.44 (s, 3, methyl protons of toluene moiety), 1.40 (s, 9, protons of t-butyl moiety); i.r. (CHCl$_3$) 3435, 3019, 1753, 1711, 1502, 1369, 1351, 1250, 1215, 1190, 1177 cm$^{-1}$; m.s.: 279, 210, 172, 91, 41;

Anal. Calcd. for C$_{16}$H$_{23}$NO$_7$S: Theory: C, 51.19; H, 6.71; N, 3.73; S, 8.54. Found: C, 51.05; H, 6.50; N, 3.63; S, 8.13.

Preparation 2

4-(R,S)-(t-Butoxycarbonylamino)-3-Oxo-1,2-Diazolidine

Under a nitrogen atmosphere, dry methylene chloride (50 ml) was cooled in an ice bath and anhydrous hydrazine (97%, 11.0 g, 333 mmole) was added. The ice bath was removed and the solution was stirred until it warmed to room temperature. At this time a solution of methyl 3-(p-toluenesulfonate)-2-(S)-(t-butoxycarbonylamino)propionate (20.0 g, 53.6 mmole) in dry methylene chloride (50 ml) was gradually added. The reaction solution was stirred under nitrogen at room temperature for 5 hours. The solution was then concentrated under reduced pressure and the concentrate was taken up in saturated aqueous sodium bicarbonate solution. The aqueous solution was continuously extracted for 14 hours with methylene chloride (700 ml). The methylene chloride solution was dried over sodium sulfate, filtered and concentrated under reduced pressure to yield approximately 5.15 g, 48% of 4-(R,S)-(t-butoxycarbonylamino)-3-oxo-1,2-diazolidine: n.m.r. (CDCl$_3$, 90 MHz): δ 7.04. (m, 1), 5.12 (m, 1), 4.28 (m, 1, C-4 proton), 3.94 (m, 1, C-5 proton), 3.20 (m, 1, C-5 proton), 1.45 (s, 9, t-butyl protons); i.r. (CHCl$_3$) 3430, 3250, 3019, 2983, 1702, 1545, 1503, 1370, 1297, 1241, 1215, 1165 cm$^{-1}$; f.d.m.s.: M+201.

Anal. Calcd. for C$_8$H$_{15}$N$_3$O$_3$: Theory: C, 47.75; H, 7.51; N, 20.88. Found: C, 47.80; H, 7.56; N, 20.61.

Preparation 3

4-(R,S)-(t-Butoxycarbonylamino)-3-Oxo-1,2-Diazolidine p-Toluenesulfonate Salt 4-(R,S)-(t-Butoxycarbonylamino)-3-oxo-1,2-diazolidine (1.7 g, 8.45 mmol) was slurried in methylene chloride (50 ml). p-Toluenesulfonic acid hydrate (1.6 g, 8.45 mmol) was added to the slurry. After 20 minutes the resultant solid material was collected then dried in vacuo for approximately 48 hours to yield 2.95 g of colorless 4-(R,S)-(t-butoxycarbonylamino)-3-oxo-1,2-diazolidine p-toluenesulfonate salt: n.m.r. (90 MHz, DMSO-d$_6$) δ 7.5 (d, 2, J=8), 7.1 (d, 2, J=8), 4.32 (m, 1), 3.9 (m, 1), 3.4 (m, 1) 2.3 (s, 3), 1.4 (s, 9); i.r. (KBr): 1742, 1704, 1537 cm$^{-1}$.

Preparation 4

4-(R,S)-(t-Butoxycarbonylamino)-3-Oxo-1-(Dimethylmethylene)-1,2-Pyrazolidinium Ylide 4-(R,S)-(t-Butoxycarbonylamino)-3-oxo-1,2-diazolidine (2.01 g, 10 mmol) was dissolved in methanol (20 ml). To this solution was added acetone dimethyl acetal (10 mmol) and d-10-camphorsulfonic acid (approx. 5 mg). The mixture was refluxed for 1.5 hours then concentrated in vacuo. The concentrate was recrystallized from dichloromethane/isopropyl ether to give 2.01 g of 4-(R,S)-(t-butoxycarbonylamino)-3-oxo-1-(dimethylmethylene)-1,2-pyrazolidinium ylide: n.m.r. (270 MHz, DMSO-$d_6$) δ 7.2 (d, 1, J=6), 4.54 (t, 1, J=10), 4.28 (m, 1), 3.85 (m, 1), 2.25 (s, 3), 2.18 (s, 3), 1.4 (s, 9); i.r. (KBr): 3232, 1692, 1671, 1608 cm$^{-1}$; m.s.: M$^+$=241.

Preparation 5

4-(R,S)-(t-Butoxycarbonylamino)-3-Oxo-1-(Methylene)-1,2-Pyrazolidinium Ylide 4-(R,S)-(t-Butoxycarbonylamino)-3-oxo-1,2-diazolidine (4.02 g, 20 mmol) was dissolved in dry methanol (50 ml). 37% Aqueous formaldehyde (1.62 g, 20 mmol) was added, the mixture was stirred for 20 minutes at room temperature then concentrated in vacuo. The solvent was then azeotropically distilled several times with methanol in vacuo at 40° C. The resultant residue was dried in vacuo at 40° C. overnight to yield 4-(R,S)-(t-butoxycarbonylamino)-3-oxo-1-(methylene)-1,2-pyrazolidinium ylide: n.m.r. (90 MHz, CDCl$_3$) δ6.1–5.3 (m, 1), 4.9–4.2 (m, 3), 4.0–3.6 (m, 1), 3.5–3.1 (m, 1), 1.4 (s, 9); i.r. (KBr): 3379, 2980, 2930, 1705, 1524, 1519, 1504, 1455, 1393, 1368, 1297, 1252, 1166 cm$^{-1}$; f.d.m.s.: M$^\oplus$=213.

Preparation 6 n-Propyl 2-Bromoacetate

Under a nitrogen atmosphere, n-propanol (30 ml, 0.4 mol) was dissolved in diethyl ether (200 ml). The solution was cooled to 0° C. then pyridine (15.82 g, 16.2 ml) was syringed into the solution. Bromoacetyl bromide (17.4 ml, 0.2 mol) was added in a rapid dropwise fashion. The resultant thick white suspension was stirred and allowed to come to room temperature over a 2.5 hour period. The solid component of the suspension was removed by filtration and washed with diethyl ether. The filtrate was evaporated in vacuo to an oil. The oil was distilled in vacuo and the fraction boiling at 56° C. collected to give 28.7 g, 79% yield of the n-propyl 2-bromoacetate: n.m.r. 90 MHz, CDCl$_3$): δ 0.95 (t, J=7.2, 3), 1.51–1.91 (m, 2); 3.79 (s, 2), 4.08 (t, J=7.2, 2).

Preparation 7 n-Propyl 2-(Dimethylphosphonato)acetate n-Propyl-2-bromoacetate (27.15 g, 0.15 mol) was dissolved in toluene (25 ml) and trimethylphosphite (17.7 ml, 18.6 g) was added. The resultant solution was heated to reflux for 5 hours then evaporated to dryness in vacuo to give 32 g of n-propyl 2-(dimethylphosphonato)acetate: n.m.r. (300 MHz, CDCl$_3$) δ 0.97 (t, J=7.5, 3), 1.63–1.75 (m, 2), 2.99 (d, J=21, 2), 3.83 (d, J=12, 6), 4.22 (t, J=7.5, 2); i.r. (CHCl$_3$) 3007, 2856, 1732, 1275, 1117, 1060, 1040 cm$^{-1}$; f.d.m.s. (m/e): M+1$^+$=211.

Preparation 8 n-Propyl 2-(Dimethylphosphonato)Prop-2-enoate

Paraformaldehyde (6 g, 0.2 mol) and pyrrolidine (1.67 ml, 0.02 mol) were suspended in methanol (150 ml). The suspension was heated to reflux to dissolve all the solids then the solution was cooled to 0° C. n-Propyl 2-(dimethylphosphonato)acetate (32 g, 0.15 mol) was added and the resultant solution was heated to reflux under nitrogen for 7 hours, 15 minutes, and stirred at room temperature overnight. Toluene was added and the reaction mixture was distilled under vacuum. The fraction boiling at 131° C.-133° C. was collected to give 11.25 g, 34% of a clear thick oil of n-propyl 2-(dimethylphosphonato)prop- 2-enoate: n.m.r. (90 MHz, CDCl$_3$): δ 0.86 (t, J=7.2, 3), 1.42–1.82 (m, 2), 3.72 (d, J=11.7, 6), 4.09 (t, J=7.2, 2), 6.65 (dd, J=20.7 and 1.8, 1), 6.94 (dd, J=41.4 and 1.8, 1); i.r. (CHCl$_3$) 3004, 2950, 1732, 1257, 1056, 1041 cm$^{-1}$.

EXAMPLE 1

4-(R,S)-(t-Butoxycarbonylamino)-3-Oxo-1-[1'-(n-Propyl Carboxylate)-1'-(Dimethylphosphonato)eth-2'-yl]-1,2-Diazolidine Under a nitrogen atmosphere, 4-(R,S)-(t-butoxycarbonylamino)-3-oxo-1,2-diazolidine (8.14 g, 40.5 mmol) was dissolved in methanol. The solution was cooled to 0° C. then n-propyl 2-(dimethylphosphonato)prop-2-enoate (8.14 g, 40.5 mmol) was added and the solution was stirred for 2 hours and was allowed to warm to room temperature. Additional n-propyl 2-(dimethylphosphonato)prop-2-enoate (2 g) was added and the solution was stirred for an additional 30 minutes then the methanol was evaporated in vacuo. The residue was chromatographed on silica gel eluted with 1% methanol/ethyl acetate to yield 10.9 g, 64% of 4-(R,S)-(t-butoxycarbonylamino)-3-oxo-1-[1'-(n-propyl carboxylate)-1'-(dimethylphosphonato)eth-2'-yl]-1,2-diazolidine: n.m.r. (300 MHz, CDCl$_3$) δ 0.96 (t, J=7.5, 3), 1.45 (s, 9), 1.62–1.75 (m, 2), 3.83 (d, J=12, 6), 4.12 (t, J=7.5, 2), 3.08–5.10 (m, 8); i.r. (CHCl$_3$): 3019, 3000, 2970, 1729, 1709, 1270, 1257, 1165, 1057, 1041 cm$^{-1}$.

Preparation 9

2-(Allyl Carboxylate)-3-(n-Propyl Carboxylate)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(n-propyl carboxylate)-1'-(dimethylphosphonato)eth-2'-yl]-1,2-diazolidine (10.6 g, 25 mmol) was dissolved in methylene chloride (50 ml) and the solution was cooled to −78° C. Allyl oxalate acid chloride (3.7 g, 25 mmol) then bis(iso-propyl)ethylamine (8.7 ml, 50 mmol) was added and the solution was stirred at -78° C. for 15 minutes then at room temperature for 45 minutes. The solution was washed with water, dried over magnesium sulfate, filtered and evaporated in vacuo to an oil. The oil was chromatographed on silica gel eluted first with 50% ethyl acetate:hexane then with ethyl acetate to give 4.66 g, 46% yield of a thick yellow oil which crystallized on standing overnight. The solid was recrystallized from diethyl ether to give 2-(allyl carboxylate)-3-(n-propyl carboxylate)-7-(R,S)-(t-butoxycarbonylamino)-8-oxo-1,5-diazabicyclo[3.3.0]Octa-2-ene: n.m.r. (300 MHz, CDCl$_3$) δ 0.94

(t, J=7.5, 3), 1.46 (s, 9), 1.60–1.73 (m, 2), 2.80–2.93 (m, 1), 3.93, 4.37 (ABq, J=12, 2), 4.04–4.16 (m, 3), 4.66–4.92 (m, 3), 5.02–5.15 (m, 1), 5.33 (dd, 1, J=12 and 1.5), 5.44 (dd, J=16.5 and 1.5, 1), 5.92–6.07 (m, 1); i.r. (CHCl$_3$) 3018, 2970, 1750, 1707, 1393, 1283, 1162 cm$^{-1}$; u.v. (EtOH): $\lambda_{max}$=344 ($\epsilon$=8915); f.d.m.s. (m/e): M$^{30}$=409; m.p. 99°–101° C.

Anal. Calcd for C$_{19}$H$_{27}$N$_3$O$_7$: Theory: C, 55.74; H, 6.65; N, 10.26; Found: C, 55.70; H, 6.58; N, 10.11.

Preparation 10

2-(Allyl Carboxylate)-3-(n-Propyl Carboxylate)-7-(R,S)-Amino-8-Oxo-1,5-Diazabicyclo[3.3.0]Octa-2-ene Hydrochloride Under a nitrogen atmosphere, 2-(allyl carboxylate)-3-(n-propyl carboxylate)-7-(R,S)-(t-butoxycarbonylamino)-8-oxo-1,5-diazabicyclo[3.3.0]octa-2-ene (246 mg, 0.6 mmol) was dissolved in a mixture of 3N hydrochloric acid in acetic acid (10 ml) and the solution was stirred at room temperature for 10 minutes then evaporated to dryness in vacuo. The remaining solvent on the resultant yellow solid was removed by azeotropic distillation with methylene chloride (3x) then carbon tetrachloride (2x) to yield 2-(allyl carboxylate)-3-(n-propyl carboxylate)-7-(R,S)-amino-8-oxo-1,5-diazabicyclo[3.3.0]octa-2-ene hydrochloride.

Preparation 11

2-(Allyl Carboxylate)-3-(n-Propyl Carboxylate)-7-(R,S)-[2-(2-(Allyloxycarbonylamino)-thiazol-4-yl)-2-(Z)-Methoxyiminoacetamido]-8-Oxo-1,5-Diazabicyclo[3.3.0]Octa-2-ene Under a nitrogen atmosphere, 2-[2-(allyloxycarbonylamino)thiazol-4-yl]-2-(Z)-methoxyiminoacetic acid (171 mg, 0.6 mmol) was suspended in methylene chloride (4 ml) and the suspension was cooled to 0° C. 2-Chloro-4,6-dimethoxy-1,3,5-triazine (105.4 mg, 0.6 mmol) followed by N-methylmorpholine (60.7 mg, 0.6 mmol) was added and the solution was stirred at 0° C. A methylene chloride solution (5 ml) of 2-(allyl carboxylate)-3-(n-propyl carboxylate)-7-(R,S)-(amino)-8-oxo-1,5-diazabicyclo3.3.0]octa-2-ene hydrochloride (0.6 mmol) then additional methylene chloride (3 ml) and additional N-methylmorpholine (60.7 mg, 0.6 mmol) were added. The resultant solution was stirred at 0° C. then allowed to warm gradually to room temperature over 2.5 hours. The reaction mixture was washed with water (1 x), dried over magnesium sulfate, filtered and evaporated in vacuo to dryness. The residue was dissolved in methylene chloride then hexane was added to the solution to cause precipitation. The precipitate was collected by filtration to give 247 mg, 71% of 2-(allyl carboxylate)-3-(n-propyl carboxylate)-7-(R,S)-[2-Z)(allyloxycarbonylamino)thiazol-4-yl)-2-(Z)-methoxyiminoacetamido]-8-oxo-1,5-diazabicyclo[3.3.0]octa-2-ene: n.m.r. (300 MHz, CDCl$_3$): $\delta$ 0.94 (t, J=7.5, 3), 1.54–1.68 (m, 2), 3.08 (dd, J=12 and 15, 1), 3.99 (s, 3), 3.97, 4.21 (ABq, J=12, 2), 3.70–4.17 (m, 5), 4.75 (d, J=6, 2), 4.82 (t, J=6, 2), 5.31 (d, J=9, 2), 5.40 (d, J=18, 2), 5.90–6.06 (m, 2), 7.18 (s, 1), 8.04 (br. s, 1); i.r. (KBr): 3230, 2970, 2940, 1753, 1730, 1699, 1674, 1564, 1392, 1327, 1270, 1232 cm$^{-1}$; u.v. (EtOH) : $\lambda_{max}$=267 ($\epsilon$=11657), 329 ($\epsilon$=8005); f.d.m.s. (m/e): M$^+$=576; m.p. 175°–178° C.

Anal. Calcd for C$_{24}$H$_{28}$N$_6$O$_9$S$_1$: Theory: C, 50.00; H, 4.90; N, 14.58; Found: C, 50.23; H, 4.95; N, 14.82.

Preparation 12

2-(Carboxylic Acid)-3-(n-Propyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene Under a nitrogen atmosphere, tetrakis(triphenylphosphine)palladium(O) (46.2 mg, 0.04 mmol) and triphenylphosphine (10.5 mg, 0.04 mmol) was suspended in acetone (10.5 ml). The suspension was stirred for 5 minutes then an acetone solution (8 ml) of 2-(allyl carboxylate)-3-(n-propyl carboxylate)-7-(R,S)-2-(2-allyloxycarbonylamino)thiazol-4-yl)-2-(Z)-methoxyiminoacetamido]-8-oxo-1,5-diazabicyclo[3.3.0]octa-2-ene (230.4 mg, 0.4 mmol) was added and the solution was stirred at room temperature for 10 minutes then cooled to 0° C. Tri(n-butyl)tin hydride (0.22 ml, 0.8 mmol) was added and the resultant solution was stirred for one hour at 0° C. Additional tri(n-butyl)tin hydride (0.22 ml, 0.8 mmol) was added and the solution was stirred for 45 minutes at 0° C. 1N Hydrochloric acid (0.8 ml) was added, the solution was filtered and the filtrate was concentrated in vacuo. The concentrate was chromatographed on an HP-20 column that was first flushed with water (500 ml) then by acetonitrile. The product-containing fractions (acetonitrile) were evaporated to dryness in vacuo; the residue was chromatographed by medium pressure liquid chromatography on a C$_{18}$ column eluted with 10% methanol:1% ammonium acetate in water. The product-containing fractions were lyophilized to give 12.3 mg of the title product. n.m.r. (300 MHz, DMSO : $\delta$ 0.89 (t, J=7.5, 3), 1.49–1.61 (m, 2), 3.83 (s, 3), 2.85–4.05 (m, 5), 3.94 (t, J=7.5, 2), 4.87–4.99 (m, 1), 7.10 (s, 1), 7.23 (br. s, 2), 9.13 (br. d, 1, J=6); i.r. (KBr): 3191 (br), 1722, 1676, 1620, 1534, 1431, 1391, 1329, 1266 cm$^{-1}$; u.v. (EtOH): $\lambda_{max}$ =232 ($\epsilon$=13722), 309 ($\epsilon$=8622); m.p. d>150° C., f.a.b.m.s. (m/e) $M$+1=453.

Preparation 13

Benzyl 2-(Dimethylphosphonato)acetate

Under a nitrogen atmosphere, benzyl 2-bromoacetate (50 g, 0.218 mol) was dissolved in toluene (50 ml). Trimethylphosphite (25.8 ml, 0.218 mol) was added and the solution was heated to reflux for 4 hours then evaporated in vacuo to an oil. The oil was distilled under house vacuum and two fractions were collected, one with a boiling point of 55°–60° C. and the other with a boiling point of 130°–135° C. The undistilled material from this distillation constituted 39.77 g of benzyl 2-(dimethylphosphonato)acetate: n.m.r. (300 MHz, CDCl$_3$) $\delta$ 3.04 (d, J=21, 2), 3.77 (d, J=10.5, 6), 5.19 (s, 2), 7.38 (s, 5); i.r. (CHCl$_3$): 3030, 3009, 2958, 1737, 1456, 1272, 1114, 1060, 1040 cm$^{-1}$; f.d.m.s. (m/e): M$^+$=258;

Anal. Calcd for C$_{11}$H$_{15}$O$_5$: Theory: C, 51.17; H, 5.86. Found: C, 51.37; H, 5.63.

Preparation 14

Benzyl 2-(Dimethylphosphonato)prop-2-enoate

Under a nitrogen atmosphere, paraformaldehyde (0.8 g, 27 mmol) was suspended in benzene (40 ml). Acetic acid (20 ml) and pyrrolidine (0.22 ml, 2.6 mmol) were added and the mixture was heated to reflux for 30 minutes then cooled to 0° C. Benzyl 2-(dimethylphosphonato)acetate (5.15 g, 20 mmol) was added and the solution was heated to reflux for 1.5 hours in an apparatus fitted with a Dean-Stark trap. Additional paraformaldehyde (0.8 g, 27 mmol) was added and the solution was heated to reflux first for 30 minutes without the Dean-Stark trap then for one hour with the trap. Another portion of paraformaldehyde (0.8 g, 27 mmol) was added and the reflux procedure repeated. The reaction solution was concentrated in vacuo then chromatographed on silica gel eluted with 5% methanol:ethyl acetate to give 2.58 g, 48% yield of benzyl 2-(dimethylphosphonato)prop-2-enoate: n.m.r. (90 MHz, CDCl$_3$): δ 3.70 10.8, 6), 5.18 (s, 2), 6.70 (dd, J=25.2 and 1.8, 1), 7.00 (dd, J=42.3 and 1.8, 1), 7.26 (s, 5); f.d.m.s. (m/e): M$^+$ =270.

EXAMPLE 2

4-(R,S)-(t-Butoxycarbonylamino)-3-Oxo-1-[1'-(Benzyl carboxylate)-1'-(Dimethylphosphonato)Eth-2'-yl]-1,2Diazolidine Under a nitrogen atmosphere, 4-(R,S)-(t-butoxycarbonylamino)-3-oxo-1,2-diazolidine (1.12 g, 5.6 mmol) was dissolved in methanol (25 ml) and the solution was cooled to 0° C. Benzyl 2-(dimethylphosphonato)prop-2-enoate (1.6 g, 5.9 mmol) was added, the solution was stirred at 0° C., allowed to warm to room temperature over a period of 2 hours then evaporated in vacuo to an oil. The oil was flash chromatographed on silica gel eluted with 1% methanol:ethyl acetate (500 ml) then 4% methanol:ethyl acetate to yield 1.8 g, 64% of 4-(R,S)(t-butoxycarbonylamino)-3-oxo-1'-[1-(benzyl carboxylate)-1'-(dimethylphosphonato)eth-2'-yl]-1,2-diazolidine: n.m.r. (90 MHz, CDCl$_3$) δ 1.40 (s, 9), 2.60–3.88 (m, 6), 3.62 (d, J=10.8, 6); 4.10–4.70 (m, 1), 5.13 (s, 2), 4.96–5.44 (m, 1), 7.26 (s, 5); i.r. (CHCl$_3$) 3020, 1708, 1499, 1369, 1258, 1162, 1057, 1040 cm$^{-1}$; f.d.m.s. (m/e): M$^+$ =471.

Preparation 15

2-(Allyl Carboxylate)-3-(Benzyl Carboxylate)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(benzyl carboxylate)-1'-(dimethylphosphonato)eth-2'-yl]-1,2-diazolidine (1.79 g, 3.8 mmol) was dissolved in methylene chloride and the solution was cooled to 0° C. Allyl oxalate acid chloride (564 mg, 38 mmol) then bis(iso-propyl)ethylamine (1.3 ml, 7.6 mmol) were added in a dropwise fashion. The solution was allowed to warm to room temperature gradually over a period of 1.5 hours. Additional allyl oxalate acid chloride (30 mg) was added and the solution was stirred at room temperature for 1.5 hours. The solution was washed with water, dried over magnesium sulfate, filtered and evaporated in vacuo to give a residue. The residue was flash chromatographed on silica gel eluted with 50% ethyl acetate:hexane to give 1.09 g, 63% yield of a yellow oil of 2-(allyl carboxylate)-3-(benzyl carboxylate)-7-(R,S)-(t-butoxycarbonylamino)-8-oxo-1,5-diazabicyclo[3.3.0]octa-2-ene: n.m.r. (300 MHz, CDCl$_3$): 1.45 (s, 9), 2.74–2.94 (m, 1), 3.92, 4.39 (ABq, J =12, 2), 4.54–4.80 (m, 3), 5.07 (br s, 1), 5.12–5.38 (m, 5), 5.76–5.92 (m, 1), 7.28–7.43 (m, 5); i.r. (CHCl$_3$) 3020, 1750, 1724, 1500, 1385, 1370, 1280, 1167 cm$^{-1}$; f.d.m.s. (m/e): M$^+$ =457; u.v. (EtOH) λ$_{max}$ =345 (ε=5600);

Anal. Calcd for C$_{23}$H$_{27}$N$_3$O$_7$: Theory: C, 60.39; H, 5.95; N, 9.19; Found: C, 60.68; H, 6.10; N, 8.93.

Preparation 16

2-(Allyl Carboxylate)-3-(Benzyl Carboxylate)-7-(R,S)-Amino-8-Oxo-1,5-Diazabicyclo[3.3.0]Octa-2-ene Hydrochloride Under a nitrogen atmosphere, 2-(allyl carboxylate)-3-(benzyl carboxylate)-7-(R,S)-(t-butoxycarbonylamino)-8-oxo-1,5-diazabicyclo[3.3.0]octa-2-ene hydrochloride (370 mg, 0.81 mmol) was combined with a 3N hydrochloric acid solution in glacial acetic acid (15 ml) and the solution was stirred at room temperature for 25 minutes. The acid was removed in vacuo and the remaining volatiles on the resultant residue were removed by azeotropic distillation with methylene chloride (2 x) to give 2-(allyl carboxylate)-3-(benzyl carboxylate)-7-(R,S)-(amino)-8-oxo-1,5-diazabicyclo[3.3.0]octa-2-ene hydrochloride.

Preparation 17

2-(Allyl Carboxylate)-3-(Benzyl Carboxylate)-7-(R,S)-[2-(2-(Allyloxycarbonylamino) thiazol-4-yl)-2-(Z)-Methoxyiminoacetamido]-8-Oxo-1,5-Diazabicyclo[3.3.0]-Octa-2-ene Under a nitrogen atmosphere, 2-2-(allyloxycarbonylamino)thiazol-4-yl]-2-(Z)-methoxyiminoacetic acid (231 mg, 0.81 mmol) was suspended in methylene chloride (5 ml) and the suspension was cooled to 0° C. 2-Chloro-4,6-dimethoxy-1,3,5-triazine (142 mg, 0.81 mmol) followed by N-methylmorpholine (0.09 ml, 0.81 mmol) were added and the solution was stirred at 0° C. for 30 minutes. A methylene chloride solution (10 ml) of 2-(allyl carboxylate)-3-(benzyl carboxylate)-7-(R,S)-amino-8-oxo-1,5-diazabicyclo[3.3.0]octa-2-ene hydrochloride (0.81 mmol) followed by additional N-methylmorpholine (0.09 ml, 0.81 mmol) were added and the solution was stirred and allowed to warm gradually to room temperature over 1.5 hours. The methylene chloride was removed in vacuo and the resultant residue was flash chromatographed on silica gel eluted with 10% hexane:ethyl acetate to give 340 mg, 67% yield of 2-(allyl carboxylate)-3-(benzyl carboxylate)-7-(R,S)-[2-(2-(allyloxycarbonylamino)thiazol-4-yl)-2-(Z)-methoxyiminoacetamido]-8-oxo-1,5-diazabicyclo[3.3.0]-octa-2-ene: n.m.r. (90 MHz, CDCl$_3$) δ 3.08 (dd, J=10.8 and 10.8, 1), 3.96 (s, 3), 3.99, 4.43 (ABq, J=12.6, 2), 3.88–4.28 (m, 2), 4.56–4.92 (m, 4), 5.16 (s, 2), 5.23 (d, J=9, 2), 5.42 (d, J=10.8, 2), 5.50–6.16 (m, 2), 7.10 (s, 1), 7.28 (br. s, 5), 8.09 (br. d, 1), 9.38 (br. s, 1); i.r. (CDCl$_3$): 3025, 1731, 1704, 1557, 1386, 1369, 1277 cm$^{-1}$ d.m.s. (m/e): M$^+$ +1 =625; u.v. (EtOH): λ$_{max}$ =264 (ε=10926), 338 (ε=6493); Anal. Calcd for C$_{28}$H$_{28}$N$_6$O$_9$S$_1$: Theory: C, 53.84; H, 4.52; N, 13.45; Found: C, 53.68; H, 4.59; N, 13.21.

Preparation 18

2-(Carboxylic Acid)-3-(Benzyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene Under a nitrogen atmosphere, 2-(allyl carboxylate)-3-(benzyl carboxylate)-7-(R,S)-(2-allyloxycarbonylamino)thiazol-4-yl)-2-(Z)-methoxyimino acetamindo]-8-oxo-1,5-diazabicyclo[3.3.0]octa-2ene (340 mg, 0.54 mmol) was suspended in a mixture of acetonitrile (10 ml) and diethyl ether (5 ml) then palladium (II) acetate (6.1 mg, 0.027 mmol,) and triphenylphosphine (56.7 mg, 0.216 mmol,) were added. Acetone (20 ml) was added and the resultant solution was stirred for 30 minutes at room temperature then cooled to 0° C. Tri(n-butyl)tin hydride (0.3 ml, 1.1 mmol) was added and the solution was stirred for 1.5 hours at room temperature. 12N hydrochloric acid (0.09 ml, 1.1 mmol) was added and the solution was concentrated in vacuo. chloride, diethyl ether was added to effect precipitation and the precipitate was collected by filtration to give 2-(carboxylic acid)-3-(benzyl carboxylate)-7-(R,S)-[2-(2-aminothiazol-4-yl)-2-(Z)-methoxyiminoacetamido]-8-oxo-1,5-diazabicyclo[3.3.0]octa-2-ene: n.m.r. (90 MHz, DMSO-d$_6$): δ 2.60–4.14 (m, 5), 3.76 (s, 3), 4.64–5.20 (m, 2), 5.04 (s, 2), 7.12 (br. s, 2), 7.24 (br. s, 5), 9.01 (br. d, 1, J=7); i.r. (KBr): 3417, 1696, 1662, 1617, 1521, 1442, 1396, 1380, 1331, 1272 cm$^{-1}$; u.v. (EtOH) $\lambda_{max}$ =231 (ε=15547), 329 (ε=11296); m.p. d>160° C., f.a.b.m.s. (m/e) M+1=501.

Preparation 19

4-(Dimethylphosphonato)butan-3-one

Under a nitrogen atmosphere, O,O -(dimethyl) methyl phosphonate (32.5 ml, 300 mmol) was dissolved in THF (450 ml) and then triphenylmethane (20–30 mg) was added. The solution was cooled to −78° C. and n-butyl lithium (1.54 M in hexane, 195 ml, 300 mmol) was added in a dropwise fashion. Additional n-butyl lithium (50 ml) was added followed by the addition of methyl propionate (26.4 g, 28.9 ml, 300 mmol) over a 15 minute period. The resultant solution was stirred at −78° C. for 75 minutes then the solution was allowed to warm to 0° C. over 75 minutes. The solution was quenched with water (250 ml), extracted with diethyl ether (2x) and the layers were separated. The aqueous layer was acidified to pH 3.0 by the addition of concentrated hydrochloric acid and extracted with diethyl ether (2x) and methylene chloride (2x). The organic extracts were combined, dried over magnesium sulfate and evaporated to dryness. The residue was distilled in vacuo and the fraction boiling at 125° C. constituted 20.3 g, 41% yield of 4-(dimethylphosphonato)butan-3-one n.m.r. (300 MHz, CDCl$_3$) δ 1.08 (t, J=7.5, 3), 2.64 (q, J=7.5, 2), 3.10 (d, J=21 and 2), 3.80 (d, J=12 and 6); i.r. (CHCl$_3$): 3007, 2950, 1717, 1262, 1251, 1186, 1061, 1038, 880, 815 cm$^{-1}$; f.d.m.s. (m/e): M=180;

Anal. Calcd for C$_6$H$_{13}$O$_4$P: Theory: C, 40.01, H, 7.27; Found: C, 39.68; H, 7.14.

Preparation 20

4-(Dimethylphosphonato)pent-4-en-3-one

Under a nitrogen atmosphere, paraformaldehyde (2.43 g, 81 mmol) was suspended in benzene. Acetic acid (50 ml) and pyrrolidine (0.58 g, 0.68 ml, 8.1 mmol) were added to the suspension and the mixture was heated to reflux for 10 minutes then cooled to 0° C. 4-(Dimethylphosphonato)butan-3-one (10 g, 61 mmol) was added and the mixture was first heated to reflux for 5 minutes then refluxed in an apparatus fitted with a Dean-Stark trap for 20 minutes. The reaction solution was concentrated in vacuo and the remaining volatiles were removed by azeotropic distillation with toluene (5x). The distillation yielded 13 g of 4-(dimethylphosphonato)pent-4-en-3-one. n.m.r. (90 MHz, CDCl$_3$): δ 1.08 (t, J=7.2 , 3), 2.74 (q, J=7.2, 2), 3.76 (d, J=10.8, 6), 6.46–7.18 (m, 2).

EXAMPLE 3

4-(R,S)-(t-Butoxycarbonylamino)-3-Oxo-1-[4'-(Dimethylphosphonato)-3'-Oxopentan-5'-yl]-1,2-Diazolidine Under a nitrogen atmosphere, 4-(R,S)-(t-butoxycarbonylamino)-3-oxo-1,2-diazolidine (12.3 g, 61 mmol) was dissolved in methanol (250 ml) and the solution was cooled to 0° C. 4-(Dimethylphosphonato)pent-4-en-3-one (61 mmol) was added and the solution was stirred at room temperature overnight. The methanol was evaporated in vacuo and the resultant oil was flash chromatographed on silica gel eluted with 50% ethyl acetate:hexane to give 8.3 g of 4-(R,S)-(t-butoxycarbonylamino)-3-oxo-1-[4'-(dimethylphosphonato)-3'-oxopentan-5'-yl]-1,2-diazolidine:n.m.r. (90 MHz, CDCl$_3$): δ 1.07 (t, J=7.2, 3), 1.44 (s, 9), 2.50–4.82 (m, 8), 3.74 (d, J=11.7, 6), 5.30 (br. s, 1).

Preparation 21

2-(Allyl carboxylate)-3-(Propionyl)-7-(R,S)-(t-Butoxycarbonylamino)-8-Oxo-1,5-Diazabicyclo[3.3.0]-Octa-2-ene Under a nitrogen atmosphere, 4-(R,S)-(t-butoxycarbonylamino)-3-oxo-1-[4'-(dimethylphosphonato)-3'-oxo-pentan-5'-yl]-1,2-diazolidine (8 g, 20 mmol) dissolved in methylene chloride (50 ml). The solution was cooled to 0° C. then allyl oxalate acid chloride (2.97 g) and bis(iso-propyl)ethylamine (5.17 g, 7 ml, 40 mmol) were added to the solution in a dropwise fashion. The solution was allowed to warm to room temperature gradually over 1.5 hours. The solution was washed with water (2x), dried over magnesium sulfate, filtered and evaporated to give a yellow oil. The oil was flash chromatographed on silica gel eluted with 50% ethyl acetate:hexane to give 1.4 g of a solid. The solid was recrystallized from a diethyl ether/hexane mixture to give 2-(allyl carboxylate)-3-(propionyl)-7-(R,S)-(t-butoxycarbonylamino)-8-oxo-1,5-diazabicyclo[3.3.0]octa-2-ene: n.m.r. (90 MHz, CDCl$_3$) δ 1.06 (t, J=7.2, 3), 1.42 (s, 9), 2.40–2.68 (m, 2), 2.83 (dd, J=9 and 10.8, 1), 3.90, 4.38 (ABq, J=10.8, 2), 3.94–4.16 (m, 1), 4.54–5.24 (m, 4), 5.26–5.62 (m, 2), 6.16–7.26 (m, 1); i.r. (CHCl$_3$): 3021, 1716, 1503, 1418, 1380, 1354, 1272, 1161; f.d.m.s. (m/e): M$^+$=379; u.v.: (EtOH) $\lambda_{max}$ =224 (ε=7600), 364 (ε=8100); m.p. 129°–130° C.

Anal. Calcd for C$_{18}$H$_{25}$N$_3$O$_6$: Theory: C, 56.98; H, 6.64; N, 11.08; Found: C, 56.73; H, 6.89, N, 11.01.

Preparation 22

2-(Allyl carboxylate)-3-(Propionyl)-7-(R,S)-Amino-8-Oxo-1,5-Diazabicyclo[3.3.0]Octa-2-ene Hydrochloride Under a nitrogen atmosphere, 2-(allyl carboxylate)-3-(propionyl)-7-(R,S)-(t-butoxycarbonylamino)-8-oxo-1,5-diazabicyclo[3.3.0]octa-2-ene (330 mg, 0.87 mmol) was combined with 3N hydrochloric acid in glacial acetic acid (15 ml). The solution was stirred for 25 minutes at room temperature then concentrated in vacuo. The remaining volatiles on the concentrate were removed by azeotropic distillation with methylene chloride (2 x) to yield 2-(allyl carboxylate)-3-(propionyl)-7-(R,S)-amino-8-oxo-1,5-diazabicyclo[3.3.0]octa-2-ene hydrochloride.

Preparation 23

2-(Allyl Carboxylate)-3-(Propionyl)-7-(R,S) [2-(2-(Allyloxycarbonylamino)thiazol-4-yl)-2-(Z)-Methoxyiminoacetamido]-8-Oxo-1,5-Diazabicyclo[3.3.0]Octa-2-ene Under a nitrogen atmosphere, 2-[2-(allyloxycarbonylamino)thiazol-4'-yl]-2-(Z)-methoxyiminoacetic acid (248 mg, 0.87 mmol) was suspended in methylene chloride (5 ml) and the suspension was cooled to 0° C. 2-Chloro-4,6-dimethoxy-1,3,5-triazine (153 mg, 0.87 mmol) then N-methylmorpholine (0.095 ml, 0.87 mmol) were added and the resultant solution was stirred at 0° C. for 30 minutes. A methylene chloride solution (10 ml) of 2-(allyl carboxylate)-3-(propionyl)-7-(R,S)-amino-8-oxo-1,5-diazabicyclo[3.3.0]octa-2-ene hydrochloride (0.87 mmol) was added followed by the addition of N-methylmorpholine (0.095 ml, 0.87 mmol). The solution was allowed to warm gradually to room temperature over 1.5 hours and then the methylene chloride was removed in vacuo. The resultant residue was flash chromatographed on silica gel eluted with 10% hexane:ethyl acetate to give 270 mg, 57% yield of 2-(allyl carboxylate)-3-(propionyl)-7-(R,S)-[2-(2-(allyloxycarbonylamino) thiazol-4-yl)-2-(Z)-methoxyiminoacetamido]-8-oxo-1,5-diazabicyclo[3.3.0]octa-2-ene: n.m.r. MHz, CDCl$_3$): δ 1.11 (t, 3, J =7.2), 2.39–2.79 (m, 2), 3.09 (dd, 1, J=9 and 11.7), 3.95 (s, 3), 3.80–4.24 (m, 3), 4.42 (½ABq, 1, J=12.5), 4.60–4.96 (m, 4), 5.16–5.68 (m, 4), 5.72–6.22 (m, 2), 7.09 (s, 1), 8.28 (br.d, 1, J=7.2), 9.55 (br.s, 1); i.r. (CHCl$_3$): 3230, 1733, 1679, 1554, 1423, 1377, 1353, 1044 cm$^{-1}$; u.v. (EtOH): $\lambda_{max}$=208 (ε=21522), 228 (ε=22084), 261 (ε=13612), 365 (ε=8122); f.d.m.s. (m/e): M$^+$+1=547; m.p. 183°–186° C.

Anal. Calcd for C$_{23}$H$_{26}$N$_6$O$_8$S: Theory: C, 50.54; H, 4.80; N, 15.38; Found: C, 50.28; H, 4.82; N, 15.43.

Preparation 24

2-(Carboxylic acid)-3-(Propionyl)-7-(R,S)-[2-(2-Aminothiazol-4-yl)-2'-(Z)-Methoxyiminoacetamido]-8-Oxo-1,5-Diazabicyclo[3.3.0]Octa-2-ene Under a nitrogen atmosphere, 2-(allyl carboxylate)-3-(propionyl)-7-(R,S)-[2-(2-(allyloxycarbonylamino)-thiazol-4-yl)-2-(Z)-methoxyiminoacetamido]-8-oxo-1,5-diazabicyclo[3.3.0]octa-2-ene (270 mg, 0.49 mmol) was suspended in a mixture of acetonitrile (10 ml)/diethyl ether (5 ml). Palladium(II) acetate (5.5 mg, 0.0245 mmol) and triphenylphosphine (51.4 mg, 0.196 mmol) were added to the suspension then acetone (45 ml) was added to effect solution and the resultant solution was stirred for 30 minutes at room temperature then cooled to 0° C. Tri(n-butyl)tin hydride (291.05 mg, 0.27 ml, 1 mmol) was added and the resultant solution was stirred at room temperature for 3 hours. Concentrated hydrochloric acid (12 M, 0.08 ml, 1 mmol) was added and the solution was concentrated in vacuo. The concentrate was dissolved in methylene chloride, precipitation was effected by the addition of diethyl ether and the precipitate was collected by filtration. The precipitate was chromatographed by medium pressure liquid chromatography on a C$_{18}$ column eluted with 10% acetonitrile/1% acetic acid in water. The product-containing fractions were lyophilized to give 43 mg (21%) of 2-(carboxylic acid-3-(propionyl)-7-(R,S)-[2-(2-aminothiazol-4-yl)-2-(Z)-methoxyiminoacetamido]-8-oxo-1,5-diazabicyclo[3.3.0]octa-2-ene: n.m.r. (300 MHz, DMSO-d$_6$: δ 0.92 (t, 3, J=6, 2.97 (dd, 1, J=6, 12), 2.46–2.48 (m, 2), 3.83 (s, 3), 3.00–4.20 (m, 3), 4.92–5.06 (m, 1), 7.03 (s, 1), 7.24 (br. s, 2), 9.15 (d, 1, J=9); i.r. (KBr) 3310 (br), 1716, 1636, 1534, 1414, 1380, 1257, 1050 cm$^{-1}$; u.v. (EtOH) $\lambda_{max}$ =233 (ε=15992), 300 (ε=6987), 350 (ε=9801); m.p.>260° C.; f.a.b.m.s. (m/e) M$^+$+1 =423.

Preparation 25

1-Fluoro-3-(Dimethylphosphonate)propan-2-one

Under a nitrogen atmosphere, O,O-(dimethyl) methylphosphonate (37.2 g, 32.5 ml, 300 mmol) was combined with THF (450 ml) and the resultant solution was cooled −78° C. n-Butyl lithium (1.54 M in hexane, 220 ml, 340 mmol) was added in a dropwise fashion and the resultant suspension was cooled to −78° C. Ethyl mono-fluoroacetate (31.8 g, 29 ml, 300 mmol) was added over 20 minutes and the solution was stirred at −78° C. for one hour then quenched with water (50 ml). The solution was stirred at room temperature for 1.5 hours then additional water (100 ml) was added and the reaction solution was extracted with diethyl ether (2x). The layers were separated and the aqueous layer was acidified to pH 3.0 by the addition of concentrated hydrochloric acid then extracted with methylene chloride (2x). The methylene chloride extracts were combined, dried over magnesium sulfate, and concentrated in vacuo. The concentrate was distilled under vacuum and the fraction with a boiling point of 125°–130° C. constituted 28.4 g, 52% yield of 1-fluoro-3-(dimethylphosphonato) propan-2-one: n.m.r. (300 MHz, CDCl$_3$): δ 3.26 (dd, 2, J=24 and 3), 3.83 (d, 6, J=12), 4.92 (d, 4, J=48); i.r. (CHCl$_3$): 3030, 3009, 2958, 1740, 1263, 1186, 1038, 831 cm$^{-1}$; f.d.m.s. (m/e): M$^+$=184;

Anal. Calcd for C$_5$H$_{10}$O$_4$FP Theory: C, 32.62; H, 5.48; Found: C, 32.37; H, 5.27.

Preparation 26

1-Fluoro-3-(Dimethylphosphonato)prop-4-en-2-one

Under a nitrogen atmosphere, paraformaldehyde (480 mg, 16 mmol) was suspended in benzene (20 ml) then trifluoroacetic acid (4 ml, 48 mmol) and pyrrolidine (0.134 ml, 1.6 mmol) were added. The mixture was heated to reflux to effect solution then cooled to room temperature. 1-Fluoro-3-(dimethylphosphonato)propan-2-one (2.2 g, 12 mmol) was added and the solution was heated to reflux for 20 minutes then concentrated in vacuo. Additional paraformaldehyde (480 mg, 16 mmol) was suspended in benzene (20 ml) under nitrogen. To the suspension was added acetic acid (5 ml) and pyrrolidine (0.134 ml, 1.6 mmol) and the mixture was heated to reflux for 10 minutes. The resultant solution was cooled to room temperature and added to the mixture containing the phosphonate compound. The resultant reaction mixture was heated to reflux for 25 minutes in an apparatus fitted with a Dean-Stark trap. The reaction solution was concentrated to an oil to yield 1-fluoro-3-(dimethylphosphonato)prop-4-en-2-one: n.m.r. (90 MHz, CDCl$_3$): δ3.80 (d, 6, J = 11), 5.22 (d, 2, J=47), 6.46–7.22 (m, 2).

EXAMPLE 4

4-(R,S)-(t-Butoxycarbonylamino)-3-Oxo-1-[1'-(Fluoro)-3'-(Dimethylphosphonato)butan-2'-oxo-4'-yl]-1,2-Diazolidine Under a nitrogen atmosphere, 4-(R,S)-(t-butoxycarbonylamino)-3-oxo-1,2-diazolidine (2.4 g, 12 mmol) was dissolved with heating in methanol (50 ml) then cooled to 0° C. 1-Fluoro-3-(dimethylphosphonato)prop-4-en-2-one (12 mmol) was added and the solution was stirred at room temperature for 48 hours then evaporated in vacuo. The residue was flash chromatographed on silica gel eluted with 2% methanol:ethyl acetate to give 1.1 g, 23% yield of 4-(R,S)-(t-butoxycarbonylamino)-3 -oxo-1-[1'-(fluoro)-3'-(dimethylphosphonato)butan-2'-oxo-4'-yl]-1,2-diazolidine.

Preparation 27

2-(Allyl carboxylate)-3-(Monofluroacetyl)-7-(R,S)-(t-Butoxycarbonylamino)-8-Oxo-1,5-Diazabicyclo-[3.3.0]Octa-2-ene Under a nitrogen atmosphere, 4-(R,S)-(t-butoxycarbonylamino)-3-oxo-1-[1'-(fluoro)-3'-(dimethylphosphonato) butan-2'-oxo-4'-yl]-1,2-diazolidine (1.1 g, 2.8 mmol) was dissolved in methylene chloride and the solution was cooled to 0° C. Allyl oxalate acid chloride (416 mg, 2.8 mmol) was added in one portion followed by the dropwise addition of bis(iso-propyl)ethylamine (724 mg, 0.98 ml, 5.6 mmol) and the solution was stirred for 15 minutes at room temperature then evaporated to dryness. The residue was flash chromatographed on silica gel eluted with ethyl acetate. The resultant yellow oil crystallized on standing overnight. The material was recrystallized from diethyl ether to yield approximately 200 mg of 2-(allyl carboxylate)-3-(monofluoroacetyl)-7-(R,S)-(t-butoxycarbonylamino)-8-oxo-1,5-diazabicyclo-[3.3.0]octa-2-ene. n.m.r. (300 MHz, CDCl$_3$): δ 1.46 (s, 9), 2.77-2.91 (m, 1), 4.03, 4.43 (ABq, 2, J=12), 4.09 (br. t, 1, J=9), 4.72-5.16 (m, 6), 5.36 (d, 1, J=12), 5.45 (d, 1, J=18), 5.91-6.08 (m, 1); i.r. (CHCl$_3$): 3020, 1740, 1717, 1375, 1346, 1287, 1161 cm$^{-1}$; u.v. (EtOH): $\lambda_{max}$=230 (ε=7885), 379 (ε=7589); f.d.m.s. (m/e): M+ =383; m.p. 134°-136° C.

Anal. Calcd for C$_{17}$H$_{22}$N$_3$O$_6$F: Theory: C, 53.26; H, 5.78; N, 10.96; Found: C, 53.57; H, 5.86; N, 10.74.

Preparation 28

2-(Allyl Carboxylate)-3-(Monofluoroacetyl)-7-(R,S)-Amino-8-Oxo-1,5-Diazabicyclo[3.3.0]Octa-2-ene Hydrochloride Under a nitrogen atmosphere, 2-(allyl carboxylate)-3-(monofluoroacetyl)-7-(R,S)-(t-butoxycarbonylamino)-8-oxo-1,5-diazabicyclo[3.3.0]octa-2-ene (190 mg, 0.5 mmol) was combined with 3 N hydrochloric acid in glacial acetic acid (10 ml). The solution was stirred at room temperature for 10 minutes then concentrated in vacuo. The remaining volatiles on the concentrate were removed by azeotropic distillation with methylene chloride (2 x) to give 2-(allyl carboxylate)-3-(monofluoroacetyl-7-(R,S)amino-8-oxo-1,5-diazabicyclo[3.3.0]octa-2-ene hydrochloride.

Preparation 29

2-(Allyl carboxylate)-3-(Monofluoroacetyl)-7-(R,S)-[2-(2-(Allyloxycarbonyl amino)thiazol-4-yl)-2-(Z)-Methoxyiminoacetamido]-8-Oxo-1,5-Diazabicyclo[3.30]-Oct-2-ene Under a nitrogen atmosphere, 2-[2-allyloxycarbonylamino)thiazol-4-yl]-2-(Z)-methoxyiminoacetic acid (142.5 mg, 0.5 mmol) was suspended in methylene chloride (5 ml) and the suspension was cooled to 0° C. 2-Chloro-4,6-dimethoxy-1,3,5-triazine (87.8 mg, 0.5 mmol) followed by N-methylmorpholine (0.054 ml, 0.5 mmol) was added and the solution was stirred at 0° C. for 30 minutes. A methylene chloride solution (10 ml) of 2-(allyl carboxylate)-3-(monofluoroacetyl)-7-(R,S)-amino-8-oxo-1,5-diazabicyclo[3.3.0]octa-2-ene hydrochloride (0.5 mmol) and additional N-methylmorpholine (0.054 ml, 0.5 mmol) were added. The resultant solution was allowed to warm gradually to room temperature, stirred for 1.5 hours then concentrated in vacuo. The residue was flash chromatographed on silica gel eluted with 10% hexane:ethyl acetate to yield 100 mg, 36% of 2-(allylcarboxylate)-3-(monofluoroacetyl)-7-(R,S)-[2-(2-(allyloxycarbonylamino)thiazol-4-yl)-2-(Z)-8-methoxyiminoacetamido]oxo-1,5-diazabicyclo[3.3.0]octa-2-ene; n.m.r. (300 MHz, CDCl$_3$) δ 3.05 (dd, 1, J=6 and 12), 4.00 (s, 3), 3.90-4.10 (m, 2), 4.17 (t, 1, J=7.5), 4.45 (½ABq, 1, J=12), 4.66-5.18 (m, 6), 5.24-5.50 (m, 4), 5.88-6.07 (m, 2), 7.27 (s, 1), 7.83 (br. d, 1, J=6); 9.14 (br. s, 1); i.r. (CHCl$_3$): 3019, 1735, 1678, 1553, 1378, 1045 cm$^{-1}$; u.v. (EtOH): $\lambda_{max}$=374 (ε=6110); f.d.m.s. (m/e): M+ +1=551; m.p. 178°-181° C.

Anal. Calcd for C$_{22}$H$_{23}$N$_6$O$_8$SF: Theory: C, 48.00; H, 4.21; N, 15.28; Found: C, 48.28; H, 4.23; N, 15.22.

Preparation 30

Methyl 2-(Diethylphosphonato)Prop-2-enoate

Under a nitrogen atmosphere, paraformaldehyde (9.6 g, 0.32 mol), methanol (250 ml), and pyrrolidine (2.28 g, 2.7 ml, 0.032 mmol) were combined and the mixture was heated to reflux for 2 hours. The solution was cooled and then methyl 2-(diethylphosphonato)acetate (50.0 g, 0.24 mol) was added and the solution was first heated to reflux for 7 hours then stirred at room temperature overnight. The reaction solution was concentrated in vacuo then dissolved in toluene and evaporated in vacuo several times. The residue was treated with phosphoric acid (86%, 2.5 ml) then distilled in vacuo. The fraction boiling from 115°-122° C. consisted of 12.32 g of a clear oil of methyl 2-(diethylphosphonato)prop-2-enoate. n.m.r. (90 MHz, CDCl$_3$) δ 1.36 (t, 6, J=7), 3.80 (s, 3), 4.00-4.36 (m, 4), 6.72 (dd, 1, J=22 and 1.8), 6.96 (dd, 1, J=41 and 1.8).

EXAMPLE 5

4-(R,S)-(t-Butoxycarbonylamino)-3-Oxo-1-[1'-(Methyl carboxylate)-1'-(Diethylphosphonato)eth-2'-yl]-1,2-Diazolidine Under a nitrogen atmosphere, 4-(R,S)-(t-butoxycarbonylamino)-3-oxo-1,2-diazolidine (1 g, 4.98 mmol) was dissolved in methanol (10 ml) with heating. The solution was cooled to 0° C. then a methanol solution (1 ml) of methyl 2-(diethylphosphonato)prop-2-enoate (1.1 g, 4.98 mmol) was added and the solution was stirred at room temperature overnight then concentrated in vacuo to give 1.9 g of an oil of 4-(R,S)-(t-butoxycarbonylamino)-3-oxo-1-[1'-(methyl carboxylate)-1'-(diethylphosphonato)eth-eth-2'-yl]-1,2-diazolidine: n.m.r. (90 MHz, CDCl$_3$) δ 1.28 (t, 6, J=7), 1.36 (s, 9), 2.68–4.64 (m, 10), 3.68 (s, 3), 5.48 (br. t, 1, J =7), 8.92 (br. s, 1).

Preparation 31

4-(R,S)-(t-Butoxycarbonylamino)-3-Oxo-1-[1'-(Methyl Carboxylate)-1'-(Diethylphosphonato)eth-2'-yl]-2-[Allyl oxaloyl]-1,2-Diazolidine Under a nitrogen atmosphere, 4-(R,S)-(t-butoxycarbonylamino)-3-oxo-1-[1'-(methyl carboxylate)-1'-(diethylphosphonato)eth-2'-yl]-1,2-diazolidine (1.9 g, 4.5 mmol) was dissolved in methylene chloride (15 ml). The solution was cooled to −60° C. and then a methylene chloride solution (2 ml) of allyl oxalate acid chloride (668.25 mg, 4.5 mmol) followed by bis(iso-propyl)ethylamine (581.63 mg, 4.5 mmol, 0.78 ml) were added and the resultant solution was stirred at −60° C. for 1 hour and at room temperature for 2 hours. The reaction solution was poured into water, the layers were separated, and the organic layer was dried over magnesium sulfate, filtered and concentrated in vacuo to give 2.34 g of a yellow oil. The oil was flash chromatographed on silica gel eluted with ethyl acetate to give 830 mg of a yellow oil of 4-(R,S)-(t-butoxycarbonylamino)-3-oxo-1-1'-(methyl carboxylate)-1'-(diethylphosphonato)eth-2'-yl]-2-[allyl oxaloyl]-1,2-diazolidine: n.m.r. (90 MHz, CDCl$_3$): δ 1.12–1.52 (m, 6), 1.44 (s, 9), 3.12–4.32 (m, 11), 3.76 (s, 3), 4.72 (br. d, 2, J=5), 5.12–6.16 (m, 3).

Preparation 32

2-(Allyl Carboxylate)-3-(Methyl Carboxylate)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(methyl carboxylate)-1'-diethylphosphonato)eth-2'-yl]-2-[allyl oxaloyl]-1,2-diazolidine (115 mg, 0.215 mmol) was dissolved in THF (5 ml). The solution was cooled to 0° C., sodium hydride (60% in oil, 17.2 mg of the oil, 0.43 mmol) was added, and the solution was stirred at 0° C. for 45 minutes. Saturated aqueous ammonium chloride solution then methylene chloride were added, the layers were separated, and the organic layer was dried over magnesium sulfate, filtered and concentrated in vacuo to give 78. mg of a yellow oil. The oil was flash chromatographed on silica gel eluted with 50% ethyl acetate/hexane to yield 28.3 mg of a yellow oil which slowly crystallized on standing. The crystals were 2-(allyl carboxylate)-3-(methyl carboxylate)-7-(R,S)-(t-butoxycarbonylamino)-8-oxo-1,5-diazabicyclo[3.3.0]octa-2-ene: n.m.r. (90 MHz, CDCl$_3$): δ 1.46 (s, 9), 2.90 (dd, 1, J=7 and 11), 3.68–4.20 (m, 2), 3.76 (s, 3), 3.92, 4.38 (ABq, 2, J=12.5), 4.80–5.00 (m, 2), 5.00–5.22 (br. d, 1, J =5), 5.22–5.60 (m, 2), 5.76–6.40 (m, 1).

Preparation 33

Ethyl 2-(Diethylphosphonato)prop-2-enoate

Under a nitrogen atmosphere, paraformaldehyde (9 g, 0.3 mol) and ethanol (250 ml, 3A) were combined. Pyrrolidine (2.13 g, 2.5 ml, 0.03 mol) was added and the solution was heated to reflux for 1.5 hours then cooled to room temperature, ethyl 2-(diethylphosphonato)acetate (50 g, 0.223 mol) was added and the solution was heated to reflux for 5 hours, stirred at room temperature overnight, reheated to reflux for 3.5 hours then cooled and evaporated in vacuo. The resultant light yellow oil was combined with phosphoric acid (86%, 2.5 ml) and the solution was distilled in vacuo. The fraction boiling between 120°–125° C. gave 22.74 g of ethyl 2-(diethylphosphonato)prop-2-enoate. n.m.r. (90 MHz, CDCl$_3$): δ 1.32 (t, 9, J=5.4), 4.00–4.40 (m, 6), 6.72 (dd, 1, J=20), 6.96 (dd, 1, J=41).

EXAMPLE 6

4-(R,S)-(t-Butoxycarbonylamino)-3-Oxo-1-1'-(Ethyl Carboxylate)-1'-(Diethylphosphonato)eth-2'-yl]-1,2-Diazolidine Under a nitrogen atmosphere, 4-(R,S)-(t-butoxycarbonylamino)-3-oxo-1,2-diazolidine (5 g, 24.9 mmol) was dissolved in ethanol (3A, 50 ml) with heating. The solution was cooled to 0° C. then ethyl 2-(diethylphosphonato) prop-2-enoate (5.87 g, 24.9 mmol) was rinsed into the solution with additional ethanol. The solution was stirred overnight at room temperature then concentrated in vacuo. The resultant oil was flash chromatographed on silica gel, eluted with 5% methanol/ethyl acetate to give 6.9 g of a yellow oil of 4-(R,S)-(t-butoxycarbonylamino)-3-oxo-1-[1'-ethyl carboxylate)-1'-(diethylphosphonato)eth-2'-yl]-1,2-diazolidine: n.m.r. (90 MHz, CDCl$_3$): δ 1.20–1.32 (m, 9); 1.36 (s, 9); 3.00–4.40 (m, 12); 5.08–5.36 (br. t, 1, J=5.4); 8.16–8.60 (br. d, 1); i.r. (CHCl$_3$) 3018, 3001, 1731, 1710, 1255, 1028 cm$^{-1}$; f.a.b.m.s. (m/e): M$^+$+1=438.

Preparation 34

4-(R,S)-(t-Butoxycarbonylamino)-3-Oxo-1-[1'-(Ethyl carboxylate)-1'-(Diethylphosphonato)eth-2'-yl]-2-[Allyl oxaloyl]-1,2-Diazolidine Under a nitrogen atmosphere, 4-(R,S)-(t-butoxycarbonylamino)-3-oxo-1-[1'-(ethyl carboxylate)-1'-(diethylphosphonato)eth-2'-yl]-1,2-diazolidine (6.5 g, 14.9 mmol) was dissolved in methylene chloride (50 ml) and the solution was cooled to −78° C. A methylene chloride solution (5 ml) of allyl oxalate acid chloride (2.21 g, 14.9 mmol) then bis(iso-propyl)ethylamine (1.93 g, 14.9 mmol) were added and the solution was stirred at −78° C. for 2.66 hours then at room temperature for 75 minutes. The solution was poured into water, the layers were separated and the organic phase was dried over magnesium sulfate, filtered and concentrated in vacuo to give 8.24 g of a golden oil. The oil was flash chromatographed on silica eluted with ethyl acetate to yield 3.87 g of a golden oil of 4-(R,S)-(t-butoxycarbonylamino)-3-oxo-1-[1'-(ethyl carboxylate)-1'-(diethylphosphanato) eth-2'-yl]-2-[allyl oxaloyl]-1,2-diazolidine: n.m.r. (90 MHz, CDCl$_3$): δ 1.20–1.36(m, 9); 1.40 (s, 9); 3.20–4.40 (m, 13); 4.60–4.88 (br. d, 2, J=5.4); 5.12–5.52 (m, 2); 5.64–6.40 (m, 1).

Preparation 35

2-(Allyl carboxylate)-3-(Ethyl carboxylate)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(ethyl carboxylate)-1'-(diethylphosphonato eth-2'-yl]-2-[allyl oxaloyl]-1,2-diazolidine (3.75 g, 6.83 mmol) was dissolved in THF (100 ml) and the solution was cooled to 0° C. Sodium hydride (60% in oil, 546.5 mg of the oil, 13.66 mmol) was added and the solution was stirred at 0° C. for 15 minutes, at room temperature for 30 minutes then cooled to 0° C. and additional THF (100 ml) was added. The solution was stirred at room temperature overnight, methylene chloride was added and saturated aqueous ammonium chloride solution (30 ml) was added. Water and additional methylene chloride was added, the layers were separated and the aqueous layer was washed with additional methylene chloride. The organic layers were combined, dried over magnesium sulfate, filtered and concentrated in vacuo to yield 2.56 g of a yellow oil. The oil was flash chromatographed on silica gel, eluted with 50% ethyl acetate/hexane as an oil which crystallized on standing to give 1.82 g, 67.5% of 2-(allyl carboxylate)-3-(ethyl carboxylate)-7-(R,S)-(t-butoxycarbonylamino)-8-oxo-1,5-diazabicyclo[3.3.0]octa-2-ene. n.m.r. (300 MHz, CDCl$_3$): δ 1.26 t, 3, J=6), 1.46 (s,9); 2.84 (m, 1), 3.91, 4.36 (ABq, 2, J=12), 4.02–4.12 (m, 1), 4.21 (q, 2, J=6), 4.66–4.92 (m, 3), 5.08 (br. s, 1), 5.32 (d, 1, J =9), 5.44 (d, 1, J =18), 5.90–6.06 (m, 1); i.r.: (CHCl$_3$) 3021, 2980, 1750, 1707, 1393, 1370, 1283, 1233, 1207, 1163 cm$^{-1}$; f.d.m.s. (m/e): M$^+$=395; u.v. (EtOH): λ$_{max}$ =345 (ε=8825); m.p. 118°–121° C.

Anal. Calcd for C$_{18}$H$_{25}$N$_3$O$_7$: Theory: C, 54.68; H, 6.37; N, 10.63; Found: C, 54.99; H, 6.55; N, 10.36.

Preparation 36

2-(Allyl carboxylate)-3-(Ethyl carboxylate)-7-(R,S)-Amino-8-Oxo-1,5-Diazabicyclo[3.3.0]Octa-2-ene Hydrochloride Under a nitrogen atmosphere, 2-(allyl carboxylate)-3-(ethyl carboxylate)-7-(R,S)-(t-butoxycarbonylamino)-8-oxo-1,5-diazabicyclo[3.3.0]octa-2-ene (120 mg, 0.304 mmol) was combined with 3N hydrochloric acid in glacial acetic acid (5 ml) and the solution was stirred for 5 minutes then concentrated in vacuo. The resultant oil was dried in vacuo for 1.6 hours to yield 2-(allyl carboxylate)-3-(ethyl carboxylate)-7-(R,S)-amino-8-oxo-1,5-diazabicyclo[3.3.0]octa-2-ene hydrochloride.

Preparation 37

2-(Allyl carboxylate)-3-(Ethyl carboxylate)-7-(R,S)-[2-(2-(allyloxycarbonylamino)-Thiazol-4-yl)-2-(Z)-Methoxyiminoacetamido]-8-Oxo-1,5-Diazabicyclo[3.3.0]-Octa-2-ene Under a nitrogen atmosphere, 2-[2'-(allyloxycarbonylamino)thiazol-4'-yl]-2-(Z)-methoxyiminoacetic acid (86.73 mg, 0.304 mmol) was slurried in methylene chloride (2 ml) and the slurry was cooled to 0° C. 2-Chloro-4,6-dimethoxy-1,3,5-triazine (53.38 mg, 0.304 mmol) then N-methylmorpholine (30.75 mg, 33.4 μl, 0.304 mmol) were added and the reaction solution was stirred for 40 minutes at 0° C. A methylene chloride solution (2.5 ml) of 2-(allyl carboxylate)-3-(ethyl carboxylate)-7-(R,S)-amino-8-oxo-1,5-diazabicyclo[3.3.0]octa-2-ene hydrochloride (0.304 mmol) then additional N-methylmorpholine (33.4 μl ) were added and the solution was stirred at 0° C. for 20 minutes and at room temperature for 2.33 hours then concentrated in vacuo. The residue was flash chromatographed on silica gel (15 mm×11 inch column) eluted with ethyl acetate to give 89.5 g of a yellow solid. The solid was taken up in a warm mixture of ethyl acetate and methylene chloride and the resultant crystals were collected by filtration to give 71.5 mg of 2-(allyl carboxylate)-3-(ethyl carboxylate)-7-(R,S)-[2-(2-(allyloxycarbonylamino)-thiazol-4-yl)-2-(Z)-methoxyiminoacetamido]-8-oxo-1,5-diazabicyclo[3.3.0]octa-2-ene: n.m.r. (300 MHz, CDCl$_3$): δ1.27 (t, 3, J=6), 3.07 (dd, 1, J=6 and 12), 3.99 (s, 3), 3.97, 4.41 (ABq, 2, J=12), 4.14 (t, 1, J=9), 4.23 (q, 2, J=6), 4.70–4.92 (m, 4), 5.28–5.52 (m, 5), 5.90–6.08 (m, 2), 7.28 (s, 1), 8.08 (br. s, 1), 9.40 (br. s, 1); i.r. (CHCl$_3$): 3021, 1750, 1730, 1701, 1554, 1226 cm$^{-1}$; f.d.m.s. (m/e): M$^+$=562; u.v. (EtOH): λ$_{max}$=209 (ε=24594), 264 (ε=13970), 343 (ε=9105); m.p. 204°–207° C. (d);

Anal. Calcd for C$_{23}$H$_{26}$N$_6$O$_9$S$_1$: Theory: C, 49.11; H, 4.66; N, 14.94; Found: C, 49.33; H, 4.64; N, 14.90.

Preparation 38

2-(Carboxylic Acid)-3-(Ethyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene Under an argon atmosphere, 2-(allyl carboxylate)-3-(ethyl carboxylate)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene (71.5 mg, 0.127 mmol) was combined with acetonitrile (2 ml), diethyl ether (1 ml), palladium(II) acetate (1.43 mg, 0.00635 mmol) and triphenylphosphine (13.32 mg, 0.0508 mmol). The resultant yellow slurry was stirred and acetone was added (2 ml) to dissolve all the solids. The solution was stirred at room temperature for 40 minutes then cooled to 0° C. tri(n-Butyl)tin hydride (75.77 mg, 70.03 μl, 0.260 mmol) was added and the solution was stirred at room temperature for 1.66 hours. Hydrochloric acid (12N, 0.022 ml, 0.260 mmol) was added and the precipitate that formed was collected by filtration then washed with ether (10 ml), methylene chloride (5 ml), and diethyl ether (5 ml) to yield 42 mg of a yellow solid. The solid was dissolved in 10% acetonitrile/water with 1% ammonium acetate then chromatographed by medium pressure liquid chromatography using a C$_{18}$ reverse phase column eluted with 10% acetonitrile/water with 1% ammonium acetate. The product-containing fractions were combined and lyophilized overnight. The solid was redissolved in a small amount of water and lyophilized again to yield approximately 40 mg of 2-(carboxylic acid)-3-(ethyl carboxylate)-7-(R,S)-2-(2-aminothiazol-4-yl)-2-(Z)-methoxyiminoacetamido]-8-oxo-1,5-diazabicyclo3.3.0]octa-2-ene. n.m.r. (300 MHz, DMSO-d$_6$): δ1.13 (t, 3, J=7.5), 2.93 (dd, 1, J=9 and 12), 3.80 (s, 3), 3.20–3.85 (m, 3), 4.00–4.06 (m, 2), 4.85–5.00 (m, 1), 7.03 (s, 1), 7.10–7.60 (m, 2), 9.14 (d, 1, J=9), i.r. (KBr): 3210 (br), 1720, 1682, 1621, 1538, 1389, 1279, 1262 cm$^{-1}$; f.a.b.m.s. (m/e): M$^+$+1=439; u.v. (EtOH): λ$_{max}$ =233 (ε=15001), 326 (ε=10781); m.p. d>168° C.

Preparation 39

2-(Diethylphosphonato)Acrylonitrile

Under a nitrogen atmosphere, benzene (200 ml), acetic acid (glacial, 50 ml), paraformaldehyde (4.51 g, 0.150 mol), and pyrrolidine (1.07 g, 0.150 mol) were combined and the mixture was heated to reflux for 10 minutes then cooled to 0° C. 2-(Diethylphosphonato)acetonitrile (20 g, 0.113 mol) was added, and the solution was heated to reflux for 5 minutes. A Dean-Stark trap was added to the apparatus and the solution was heated to reflux for an additional 20 minutes then concentrated in vacuo. Three repetitions of first redissolution of the residue in toluene and then evaportion to dryness in vacuo of the resultant solution yielded 2-(diethylphosphanato)acrylonitrile; n.m.r. (90 MHz, CDCl$_3$): δ1.44 (t, 6, J=7), 3.88–4.60 (m, 4), 6.36–7.00 (m, 2).

EXAMPLE 7

4-(R,S)-(t-Butoxycarbonylamino)-3-Oxo-1-[1'-Cyano-1'-(Diethylphosphonato)eth-2'-yl]-1,2-Diazolidine Under a nitrogen atmosphere, 4-(R,S)-(t-butoxycarbonylamino)-3-oxo-1,2-diazolidine (22.7 g, 0.113 mol) was dissolved in methanol (200 ml) with heating and the solution was cooled to 0° C. 2-(Diethylphosphonato)acrylonitrile (0.113 mol) was washed into the solution with additional methanol (10 ml) and the solution was stirred at 0° C. for 1 hour then at room temperature overnight and concentrated in vacuo to an oil. The oil was flash chromatographed on silica gel eluted with 5% methanol/ethyl acetate to yield 15.83 g of 4-(R,S)-(t-butoxycarbonylamino)-3-oxo-1-[1'-cycano-1'-(diethylphosphonato)eth-2'-yl]-1,2-diazolidine: n.m.r. (90 MHz, CDCl$_3$): δ1.16–1.40 (m, 6), 1.36 (s, 9), 3.08–4.80 (m, 10), 5.34 (br. s, 1), 8.72 (br. s, 1), i.r. (CHCl$_3$): 3021, 2250, 1712, 1264, 1023 cm$^{-1}$; f.a.b.m.s. (m/e): M$^+$+1=391.

Preparation 40

2-(Allyl Carboxylate)-3-Cyano-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-cycano-1'-(diethylphosphanato)eth-2'-yl]-1,2-diazolidien (15.83 g, 0.041 mol) was dissolved in methylene chloride (250 ml) and the solution was cooled to 0° C. Allyl oxalate acid chloride (6.03 g, 0.041 mol) then bis(iso-propyl)ethylamine (10.49 g, 0.082 mol) were added, and the solution was stirred at 0° C. for 1.5 hours, washed with water (2x), dried over magnesium sulfate, filtered and concentrated to a yellow oil (16.46 g). The oil was flash chromatographed on silica gel eluted with 50% haxane in ethyl acetate to yield 3.97 g of 2-(allyl carboxylate)-3-cyano-7-(R,S)-(t-butoxycarbonylamino)-8-oxo-1,5-diazabicyclo[3.3.0]octa-2-ene. (The following data was gathered on a small amount of this final product that had been triturated with diethyl ether.) n.m.r. (300 MHz, CDCl$_3$): δ1.47 (s, 9); 2.93 (dd, 1, J=9 and 12); 3.93, 4.37 (ABq, 2, J=12); 4.09 (br. t, 1, J=9); 4.62–4.77 (m, 1); 4.78–4.96 (m, 2); 5.13 (br. s, 1); 5.36 (d, 1, J=12); 5.47 (d, 1, J=15); 5.92–6.06 (m, 1); i.r. (CHCl$_3$): 3040, 2990, 2220, 1753, 1742, 1716, 1501, 1407, 1370, 1160 cm$^{-1}$; f.d.m.s. (m/e): M$^+$=348; u.v. (EtOH) λ$_{max}$ =212 (ε=8400), 365 (ε=5300);

Anal. Calcd for C$_{16}$H$_{20}$N$_4$O$_5$: Theory: C, 55.17; H, 5.79; N, 16.08; Found: C, 55.46; H, 5.56; N, 15.95.

Preparation 41

2-(Allyl Carboxylate)-3-Cyano-7-(R,S)-Amino-8-Oxo-1,5-Diazabicyclo[3.3.0]Octa-2-ene Hydrochloride Under a nitrogen atmosphere, 2-(allyl carboxylate)-3-cyano-7-(R,S)-(t-butoxycarbonylamino)-8-oxo-1,5-diazabicyclo[3.3.0]octa-2-ene (1.54 g, 4.43 mmol) was combined with 3N hydrochloric acid in glacial acetic acid (45 ml) and the mixture was stirred at room temperature until it was a solution (5 minutes), when it was evaporated in vacuo to dryness. The residue was redissolved in methylene chloride and the solution was taken to dryness in vacuo two times to yield 2-(allyl carboxylate)-3-cyano-7-(R,S)-amino-8-oxo-1,5-diazabicyclo[3.3.0]octa-2-ene hydrochloride.

Preparation 42

2-(Allyl Carboxylate)-3-Cyano-7-(R,S)-[2-(2-Aminothiazol-4-yl)-2-(Z)-Methoxyiminoacetamido]-8-Oxo-1,5-Diazabicyclo[3.3.0]Octa-2-ene Under a nitrogen atmosphere, 2-[2'-(allyloxycarbonylamino)thiazol-4'-yl]-2-(Z)-methoxyiminoacetic acid (1.26 g, 4.43 mmol) was slurried in methylene chloride (25 ml) and the slurry was cooled to 0° C. 2-Chloro-4,6-dimethoxy-1,3,5-triazine (777 mg, 4.43 mmol) then N-methylmorpholine (0.487 ml, 4.43 mmol) was added and the mixture was stirred at 0° C. for 70 minutes. 2-(allyl carboxylate)-3-cyano-7-(R,S)-amino-8-oxo-1,5-diazabicyclo[3.3.0]octa-2-ene hydrochloride (4.43 mmol) was dissolved in methylene chloride (20 ml) and was added followed by an additional amount of N-methylmorpholine (0.49 ml). The resultant mixture was stirred at 0° C. for 1.5 hours then at room temperature overnight and concentrated to dryness in vacuo. The residue was flash chromatographed on silica gel eluted with ethyl acetate to yield 630 mg of a yellow oil. The oil was taken up in a mixture of ethyl acetate/hexane and the resultant precipitate was isolated by filtration to yield approximately 180 mg of 2-(allyl carboxylate)-3-cyano-7-(R,S)-[2-(2-aminothiazol-4-yl)-2-(Z)-methoxyiminoacetamido]-8-oxo-1,5-diazabicyclo[3.3.0]octa-2-ene: n.m.r. (300 MHz, DMSO-d$_6$): δ3.20 (dd, 1, J=12 and 12); 3.82–3.94 (m, 1); 3.88 (s, 3); 4.13, 4.41 (ABq, 2, J=15); 4.70 (d, 2, J=6); 4.85 (d, 2, J=6); 5.02–5.15 (m, 1); 5.22–5.52 (m, 4); 5.86–6.04 (m, 2); 7.44 (s, 1); 9.29 (d, 1, J=6); 12.18 (s, 1); i.r. (CHCl$_3$); 3020, 3000, 2230, 1733, 1681, 1554, 1411, 1371, 1276, 1044 cm$^{-1}$; f.d.m.s. (m/e): M$^+$=515; u.v. (EtOH) λ$_{max}$=209 (ε=22387), 227 (ε=21822), 263 (ε=4291), 363 (ε=5800);

Anal. Calcd for C$_{21}$H$_{21}$N$_7$O$_7$S$_1$: Theory: C, 48.93; H, 4.11; N, 19.02; Found: C, 49.14; H, 4.23; N, 18.77.

Preparation 43

1-(Dimethylphosphonato)-1-(Methylsulfonato)Ethylene

Under a nitrogen atmosphere, benzene (50 ml), acetic acid (15 ml), paraformaldehyde (0.99 g, 0.033 mol), and pyrrolidine (0.234 g, 0.0033 mol) were combined and the mixture was warmed to reflux for 25 minutes then cooled to 0° C. 1-(Dimethylphosphonato)-1-methylsulfonato)methane was added (5 g, 0.025 mol) and the solution was heated to reflux first for 10 minutes then a Dean-Stark trap was added to the apparatus and the solution was heated to reflux for 25 minutes. Toluene was added and the solution was concentrated in vacuo, followed by the addition of toluene and reconcentration in vacuo to yield 1-(dimethylphosphonato)-1-(methylsulfonato)ethylene: n.m.r. (90 MHz, CDCl$_3$): δ3.08 (s, 3); 3.80 (d, 6, J=13); 6.80 (d, 1, J=18); 7.00 (d, 1, J=36).

EXAMPLE 8

4-(R,S)-(t-Butoxycarbonylamino)-3-Oxo-1-[1'-(Dimethylphosphonato)-1'-(Methylsulfonato)Eth-2'-yl]-1,2-Diazolidine Under a nitrogen atmosphere, 4-(R,S)-(t-butoxycarbonylamino)-3-oxo-1,2-diazolidine (4.5 g, 22.4 mmol) was dissolved in methanol (40 ml) with warming then the solution was cooled to 0° C. 1-(Dimethylphosphonato)-1-(methylsulfonato)ethylene (25 mmol) was added and the solution was stirred for 1 hour at 0° C., for 1 hour and 50 minutes at room temperature then filtered. The solid collected by filtration was washed with methanol, dried in vacuo at room temperature overnight to give 3.25 g of 4-(R,S)-(t-butoxycarbonylamino)-3-oxo-1-[1'-(dimethylphosphonato)-1'-(methylsulfonato)eth-2'-yl]-1,2-diazolidine. n.m.r. (300 MHz, DMSO-d6): δ1.40 (s, 9); 2.80–3.00 (m, 1); 3.10–3.66 (m, 3); 3.20 (s, 3); 3.66–3.80 (m, 6); 4.20–4.54)m, 2); 7.20 (br. d, 1, J=12); 9.70 (br. d, 1, J=6); i.r. (KBr): 3310, 3190, 1710, 1696, 1525, 1232, 1165, 1142, 1052, 1043 cm⁻¹; f.d.m.s. (m/e): M+=415, 215 (M-200), 201 (M-215); m.p. 141°–143° C.;

Anal. Calcd for $C_{13}H_{26}N_3O_8S_1P_1$: Theory: C, 37.59; H, 6.31, N, 10.12; Found: C, 37.85; H, 6.30; N, 9.99.

Preparation 44

2-(Allyl Carboxylate)-3-(Methylsulfonato)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(dimethylphosphonato)-1'-(methylsulfonato)eth-2'-yl]-1,2-diazolidine (2.75 g, 6.6 mmol) was slurried in methylene chloride (150 ml) and the resulting slurry was cooled to 0° C. Allyl oxalate acid chloride (0.98 g, 6.6 mmol) was rinsed into the solution with additional methylene chloride then bis-(iso-propyl)ethylamine (1.71 g, 13.2 mmol, 2.3 ml) was added and the mixture was stirred at 0° C. for 30 minutes then at room temperature for 3.25 hours. The solution was washed with water, dried over magnesium sulfate, filtered and concentrated to yield 3.89 g of a yellow oil. The oil was combined with crude product from a previous procedure paralleling that above and the combination was flash chromatographed on silica gel eluted with 25% hexane/75% ethyl acetate to yield 1.87 g of 2-(allyl carboxylate)-3-(methylsulfonato)-7-(R,S)-(t-butoxycarbonylamino)-8-oxo-1,5-diazabicyclo[3.3.0]octa-2-ene. n.m.r. (90 MHz, CDCl3): δ1.44 (s, 9); 2.94 (dd, 1, J=11 and 11); 3.10 (s, 3); 3.86–4.90 (m, 4); 3.97, 4.49 (ABq, 2, J=12.5); 4.96–5.18 (br. d, 1, J=5); 5.18–5.54 (m, 2); 5.68–6.18 (m, 1); i.r. (CHCl3) 3021, 1741, 1717, 1326, 1142 cm⁻¹; f.d.m.s. (m/e): M+=401; u.v. (EtOH): λmax=329 (ε=6037); m.p. 80° C.

Anal. Calcd for $C_{16}H_{23}N_3O_7S_1$: Theory: C, 47.87; H, 5.78, N, 10.47; Found: C, 47.75; H, 5.74; N, 10.55.

Preparation 45

2-(Carboxylic Acid)-3-Cyano-7-(R,S)-[2-(2-Aminothiazol-4-yl)-2-(Z)-Methoxyiminoacetamido]-8-Oxo-1,5-Diazabicyclo[1,5-Diazabicyclo[3.3.0]Octa-2-ene 2-(Allyl carboxylate)-3-cyano-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene (205 mg, 0.398 mmol) was dissolved in acetonitrile (10 ml) and the stirred solution was flushed with nitrogen. Triphenylphosphine (41.76 mg, 0.159 mmol) and palladium(II) acetate (4.47 mg, 0.0199 mmol) were added and the solution was stirred under nitrogen at room temperature for 20 minutes then cooled to 0° C. Tri(n-butyl)tin hydride (237.5 mg, 0.816 mmol, 0.22 ml) was added and the solution was stirred for ten minutes at 0° C. and then at room temperature for one hour. Diethyl ether was added (10 ml) and the resultant solution was stirred for an additional hour at room temperature then additional ether (approximately 7 ml) and acetonitrile (approximately 1 ml) were added. 12 M hydrochloric acid (0.068 ml, 0.816 mmol) was added and the resultant yellow precipitate was collected by filtration, washed with diethyl ether (20 ml), dichloromethane (5 ml), and again with diethyl ether (10 ml) to yield 136 mg of a solid. The solid was chromatographed by medium pressure liquid chromatography on a $C_{18}$ reverse phase column eluted with 5% acetonitrile/1% acetic acid/water to yield approximately 15 mg of 2-(carboxylic acid)-3-cyano-7-(R,S)-[2-(2-aminothiazol-4-yl)-2-(Z)-methoxy-iminoacetamido]-8-oxo-1,5-diazabicyclo[3.3.0]octa-2-ene: n.m.r. (300 MHz, DMSO-d6): δ3.00–4.00 (m, 1); 3.09 (dd, 1, J=9 and 12), 3.84 (s, 3), 3.96 (d, J=12, 1), 4.27 (½ ABq, 1, J=12), 4.92–5.06 (m, 1), 6.98 (s, 1), 7.24 (br. s, 2), 9.15 (d, 1, J=9); i.r. (KBr): 3320 (br), 2220, 1724, 1649, 1534, 1398, 1046 cm⁻¹; u.v. (EtOH): λmax=227 (εmax=16225), 302 (εmax=9726); m.p. >225° C. (d).

Preparation 46

N-(t-Butoxycaronyl) (L)-Serine Trifluoroacetyl Acyl Hydrazide

N-(t-Butoxycarbonyl) (L)-serine acyl hydrazide (32.85 g, 150 mmol) was suspended in ethanol (400 ml). Ethylthio trifluorothioacetate (30 ml, 37.02 g, 234.3 mmol) was added to the suspension and the resultant mixture was stirred at room temperature for 65 hours. The solvent was removed in vacuo and the residue was dissolved in diethyl ether (160 ml). A seed crystal was added to the diethyl ether solution and the resultant crystals were collected by filtration (approx. 27 g). The filtrate was evaporated in vacuo and diethyl ether (50 ml) was added to the residue. The solids that formed on standing were removed by filtration to yield approximately 16.5 g of additional product. The two batches of solids collected by filtration were combined and recrystallized from diethyl ether (3 liters). After effecting solution, the solution was reduced to approximately 450 ml to yield (after a second crop) 41.04 g, 87% yield of N-(t-butoxycarbonyl) (L)-serine trifluoroacetyl acyl hydrazide: n.m.r. (300 MHz, DMSO-d6): δ11.5 (br. s, 1), 10.33 (s, 1), 6.84 (d, 1, J=9), 4.9 (t, 1, J=7, (OH), 4.1 (m, 1), 3.59 (br. m, 2), 1.4 (s, 9); specific rotation: $[\alpha]_D^{25}$ = −25.87° (10.05 mg/ml, methanol); m.p.: 143°–144° C. (first crop), 142°–144° C. (second crop).

Anal. Calcd for $C_{10}H_{16}N_3O_5F_3$: Theory: C, 38.10; H, 5.12; N, 13.33; Found: C, 38.34; H, 4.89; N, 13.16.

Preparation 47

4-(S)-(t-Butoxycarbonylamino)-1-(Trifluoro acetyl)-3-Oxo-1,2-Diazolidine

N-(t-Butoxycarbonyl) (L)-serine trifluoroacetyl acyl hydrazide (3.78 g, 12 mmol) and triphenylphosphine (3.46 g, 13.2 mmol) were dissolved in THF (50 ml). To the solution was added a THF solution (10 ml) of 95% diethyl azodicarboxylate (2.42 g, 2.19 ml, 13.2 mmol). The resultant mixture was stirred at room temperature for six hours and then the solvent was removed in vacuo. The residue was dissolved in ethyl acetate (100 ml) and then the solution was washed with aqueous sodium bicarbonate solution (33 ml, 3X). The sodium bicarbonate extracts were combined, aqueous saturated brine solution (70 ml) was added and the resultant mixture was extracted with ethyl acetate (120 ml, 3X). The sodium bicarbonate solution was then layered with additional ethyl acetate (200 ml) and 1N hydrochloric acid (approx. 80 ml) was added until the sodium bicarbonate solution had a pH of 2.5. The ethyl acetate layer was separated and the aqueous layer was extracted with additional ethyl acetate (4X, 125 ml). The ethyl acetate extracts were combined, washed with saturated aqueous brine (125 ml, 2X), dried over sodium sulfate, filtered, and taken to dryness in vacuo. The resultant residue was dissolved in acetonitrile (100 ml) then the acetonitrile was removed in vacuo. Treatment of the residue with acetonitrile was repeated to yield 3.06 g, 96% yield of 4-(S)-(t-butoxycarbonylamino)-1-(trifluoroacetyl)-3-oxo-1,2-diazolidine: n.m.r. (300 MHz, CDCl$_3$): δ5.25 (d, 1, J=6), 4.81 (t, 1), 4.6 (m, 1), 4.06 (t, 1), 1.46 (s, 9); i.r. (CHCl$_3$): 1722, 1682, 1518 cm$^{-1}$; f.d.m.s. (m/e): M$^+$=297; specific rotation: $[\alpha]_D^{25}$ = −88.14° (10.03 mg/ml in methanol);

Anal. Calcd for C$_{10}$H$_{14}$N$_3$O$_4$F$_3$: Theory: C, 40.41; H, 4.75; N, 14.14; Found: C, 40.58; H, 5.01; N, 13.92.

Preparation 48

4-(S)-(t-Butoxycarbonylamino)-3-Oxo-1,2-Diazolidine 4-(S)-(t-butoxycarbonylamino)-1-(trifluoroacetyl)3-oxo-1,2-diazolidine (2.97 g, 10 mmol) was suspended in water (30 ml), 1 N sodium hydroxide solution (20 ml, 0.8 g, 20 mmol) was added to raise the pH of the solution to 12.2 and the resultant mixture was stirred for one hour at room temperature. The pH of the mixture was adjusted to 7.2 by the addition of 1N hydrochloric acid (10 ml). Sodium chloride (13 g) was added to the solution and the mixture was extracted with chloroform (50 ml, 8X). The chloroform extracts were combined, washed with saturated aqueous sodium chloride solution (75 ml), dried over sodium sulfate, filtered, and evaporated to dryness in vacuo. Diethyl ether (100 ml) was added to the residue and then the ether was removed in vacuo to yield 0.798 g of a white solid of 4-(S)-(t-butoxycarbonylamino)-3-oxo-1,2-diazolidine: n.m.r. (300 MHz, DMSO-d$_6$) δ9.23 (s, 1), 7.04 (d, 1, J=9), 5.24 (br. s, 1,), 4.24 (m, 1), 3.41 (t, 1), 2.88 (t, 1), 1.38 s, 9); specific rotation: $[\alpha]_D^{25}$ = −74.16° (10.06 mg/ml in methanol); (the compound was dried overnight at 80° C. before analysis):

Anal. Calcd for C$_8$H$_{15}$N$_3$O$_3$: Theory: C, 47.75; H, 7.51; N, 20.88; Found: C, 47.75; H, 7.46; N, 20.62.

I claim:
1. A compound of the formula:

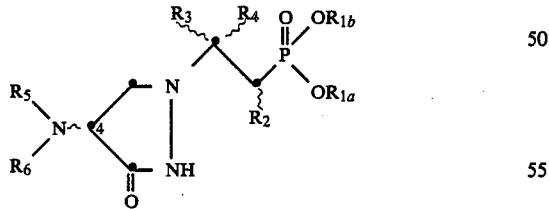

wherein:
R$_1{}^a$ and R$_1{}^b$ are the same or different and are C$_1$ to C$_6$ alkyl or phenyl;
R$_2$ is hydrogen, halo, C$_1$ to C$_6$ alkyl, C$_1$ to C$_6$ alkyl substituted by one or two halogen, hydroxy, protected hydroxy, amino, protected amino, C$_1$ to C$_7$ acyloxy, nitro, carboxy, protected carboxy, carbamoyl, carbamoyloxy, cyano, methylsulfonylamino or C$_1$ to C$_4$ alkoxy groups, perfluoro C$_2$ to C$_4$ alkyl, C$_7$ to C$_{12}$ arylalkyl group substituted on the C$_1$ to C$_6$ alkyl portion with one or two groups chosen from halogen, hydroxy, protected hydroxy, amino, protected amino, C$_1$ to C$_7$ acyloxy, nitro, carboxy, protected carboxy, carbamoyl, carbamoyloxy, cyano, N-(methylsulfonylamino) or C$_1$ to C$_4$ alkoxy; and/or the phenyl group maybe substituted with 1 or 2 groups chosen from halogen, hydroxy, protected hydroxy, nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, or an N-(methylsulfonylamino) group, phenyl, a phenyl group substituted with one or two moieties chosen from the group consisting of halogen, hydroxy, protected hydroxy, cyano, nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino), 1,3-thaizol-2-yl, 4-(protected carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-(protected carboxy)-4-methyl-1,3,4-triazxol-5-yl, 1,3-oxazxol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiadiazol-5-yl, 2-thiol-1,3,4-thiadiazol-5-yl, 2-(methylthio)-1,3,4-thaidiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(protected carboxymethyl)-1H-tetrazol-5-yl, 1-(carboxymethyl)-1H-tetrazol-5-yl sodium salt, 1-(methysulfonic acid)-1H-tetrazol-5-yl, 1-(methylsulfonic acid)-1H-tetrazol-5-yl sodium salt, 2-methyl-1H-tetrazol-5-yl, 1,2,3-trazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-trazin-3-yl, 1,4,5,6-tetrahydro-4-(formylmethyl)-5,6-dioxo-as-triazin-3-yl, 2,5-dihydro-5-oxo-6-hydroxy-as-triazin-3-yl, 2,5-dihydro-5-oxo-6-hydroxy-as-trazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin- 3-yl, 2,5-dihydro-5-oxo-as-triazin-3-yl, 2,5-dihydro-5-oxo-2-methyl-as-triazin-3-yl, 2,5-dihydro5-oxo-2,6-dimethyl-as-triazxin-3-yl, tetrazolo[1,5-b]pyridazin-6-yl and 8-aminotetrazxolo[1,5-b]pyridazin-6-yl, 4-(protected carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(protected carboxymethyl)-1H-tetrazol-5-yl, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin- 3-yl, tetrazolo[1,5-b]pyridazin-6-yl, and 8-aminotetrazolo[1,5-b]pyridazin-6-yl, nitro or cyano; a group of the formula

—CX$_3$ wherein X is fluoro, chloro, bromo or iodo; a group of the formula

wherein Z is 0, 1 or 2 and R$_7$ is C$_1$ to C$_6$ alkyl, C$_1$ to C$_6$ alkyl substituted by one or two halogen, hydroxy, protected hydroxy, amino, protected amino, C$_1$ to C$_7$ acyloxy, nitro, carboxy, protected carboxy, carbamoyl, carbamoyloxy, cyano, methylsulfonylamino or C$_1$ or C$_4$ alkoxy groups, phenyl, a phenyl group substituted with one or two moieties chosen from the group consisting of halogen, hydroxy, protected hydroxy, cyano, nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino), C$_7$ to C$_{12}$ arylalkyl, C$_7$ to C$_{12}$ arylalkyl group substituted on the C$_1$ to C$_6$ alkyl portion with one or two groups chosen from halogen, hydroxy, protected hydroxy, amino, protected amino, C$_1$ to C$_7$ acyloxy, nitro, carboxy, protected carboxy, carbamoyl, carbamoyloxy, cyano, N-(methylsulfonylamino) or C$_1$ to C$_4$ alkoxy; and/or the phenyl group may be substituted with 1 or 2 groups chosen from halogen, hydroxy, protected hydroxy, nitro, C$_1$ to C$_6$ alkyl, C$_1$ to C$_4$ alkoxy, carboxy, protected carboxy, carboxy methyl, protected carboxymethyl, hydroxymethyl, protected hydroxy methyl, aminomethyl, protected aminomethyl, or an N-(methylsulfonyamino) group, or R$_7$ is 1,3-thiazol-2-yl, 4-(protected carboxymethyl)-5-methyl-1,3-thiazol-2-yl, 1,2,4-thadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl--2-(protected carboxy)-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiadiazol- 5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(protected carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazxol-5-yl, 4-methyl-1,2,3-triazxol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, b 1,4,5,6-tetrahydro-4-(formylmethyl)-5,6-dioxo-as-triazin-3-yl, 2,5-dihydro-5-oxo-6-hydroxy-as-triazin-3-yl, 2,5-dihydro-5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-trizin- 3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo-[1,5]pyridazin-6-yl, 4-(protected carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth- 2-yl)-1H-tetrazol-5-yl, 1-(protected carboxymethyl)-1H-tetrazol-5-yl, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2methyl-as-triazin-3-yl, tetrazxolo[1,5-b]pyridazin-6-yl, and 8-aminotetrazolo[1,5-b]pyridazin-6-yl;

a group of the formula

—COR$_8$ wherein R$_8$ is hydrogen, C$_1$ to C$_6$ alkyl, C$_1$ to C$_6$ alkyl substituted by one or two halogen, hydroxy, protected hydroxy, amino, protected amino, C$_1$ to C$_7$ acyloxy, nitro, carboxy, protected carboxy, carbamoyl, carbamoyloxy, cyano, methylsulfonylamino or C$_1$ to C$_4$ alkoxy groups, perfluoro C$_2$ to C$_4$ alkyl, C$_7$ to C$_{12}$ arylalkyl group substituted on the C$_1$ to C$_6$ alkyl portion with one or two groups chosen from halogen, hydroxy, protected hydroxy, amino, protected amino, C$_1$ to C$_7$ acyloxy, nitro, carboxy, protected carboxy, carbamoyl, carbamoyloxy, cyano, N-(methylsulfonylamino) or C$_1$ to C$_4$ alkoxy; and/or the phenyl group may be substituted with 1 or 2 groups chosen from halogen, hydroxy, protected hydroxy, nitro, C$_1$ to C$_6$ alkyl, C$_1$ to C$_4$ alkoxy, carboxy, protected carboxy, carboxy methyl, protected carboxymethyl, hydroxymethyl, protected hydroxymethyl, aminomethyl, protected aminomethyl, or a N-methylsulfonylamino) group, phenyl, a phenyl group substituted with one or two moieties chosen from the group consisting of halogen, hydroy, protected hydroxy, cyano, nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, trifluoromethyl or N-(methulsulfonylamino), amino, an amino group with one substituent chosen from the group consisting of phenyl, a phenyl group substituted with one or two moieties chosen from the group consisting of halogen, hydroxy, protected hydroxy, cyano, nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino), C$_1$ to C$_6$ alkyl, and C$_7$ to C$_{12}$ aralkyl, or an amino group with two substituents chosen from the group consisting of phenyl, a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino); a group of the formula

—COOR$_9$ wherein $R_9$ is $C_1$ to $C_6$ alkyl, $C_1$ to $C_6$ alkyl substituted by one or two halogen, hydroxy, protected hydroxy, amino, proteocted amino, $C_1$ to $C_7$ acyloxy, nitro, carboxy, protected carboxy, carbamoyl, carbamoyloxy, cyano, methylsulfonylamino or $C_1$ to $C_4$ alkoxy groups, $C_7$ to $C_{12}$ arylalkyl, $C_7$ to $C_{12}$ arylalkyl group substituted on the $C_1$ to $C_6$ alkyl portion with one or two groups chosen from halogen, hydroxy, protected hydroxy, amino, protected amino, $C_1$ to $C_7$ acyloxy, nitro, carboxy, protected carboxy, carbamoyl, carbamoyloxy, cyano, N-(methylsulfonylamino) or $c_1$ to $C_4$ alkoxy; and/or the phenyl group may be substituted with 1 or 2 groups chosen from halogne, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or an N-(methylsulfonylamino) group, or $R_9$ is phenyl, a phenyl group substituted with one or two moieties chosen from the group consisting of halogen, hydroxy, protected hyddroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluorometyl or N-(methylsulfonylamino), a carboxy -protecting group, or a non-toxic, metabolically-labile, ester-forming group;

a group of the formula

—PO$_3$(R$_{10}$)$_2$ wherein $R_{10}$ is $C_1$ to $C_6$ alkyl, $C_1$ to $C_6$ alkyl substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups, $C_7$ to $C_{12}$ arylalkyl, $C_7$ to $C_{12}$ araylalkyl group substituted on the $C_1$ to $C_6$ alkyl portion with one or two groups chosen from halogen, hydroxy, protected hydroxy, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_6$ alkyl, $C_1$ to $C_4$ alkoxy, protected carboxy, carboxymethyl, protected carboxymethyl, hydroxymethyl, protected hydroxymethyl, aminomethyl, protected aminomethyl, or an N-(methylsulfonylamino) group, or $R_{10}$ is phenyl, or a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino); or a group of the formula

—CH$_2$—S—A wherein A is 1,3-thiazol-2-yl, 4-(protected carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-(protected carboxy)-4-methyl-1,3,4-triazol-5-yl, 1,3-oxazol-2-yl, 1,3,4-oxdiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4- thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(protected carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3,-triazol-5-yl, 1-methyl-1,2,3-triazol-5-yl, 2-methyl-1,2,3-triazol-5-yl, 4-methyl-1,2,3-triazxol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-as-triazin-3-yl, 2,5-dihydro- 5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]pyridazin-6-yl, 4-(protected carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(protected carboxymethyl)-1H-tetrazol-5-yl, 1-(methylsulfonic acid)-1H-tetrazol-5-yl, sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl;

$R_3$ and $R_4$ are the same or different and are hydrogen, $C_1$ to $C_6$ alkyl, $C_1$ to $C_6$ alkyl substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups, $C_7$ to $C_{12}$ arylalkyl, $C_7$ to $C_{12}$ arylalkyl group substituted on the $C_1$ to $C_6$ alkyl portion with one or two groups chosen from halogen, hydroxy, protected hydroxy, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or an N-(methylsulfonylamino) group, or $R_3$ and $R_4$ are the same or different and are phenyl, a phenyl group substituted with one or two moieties chosen from the group consisting of halogen, hydroxy protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminoethyl, trifluoromethyl or N-(methylsulfonylamino), or a group of the formula

—$COOR_{11}$ wherein $R_{11}$ has the same definition as $R_9$;
$R_5$ and $R_6$ are:
(1) each hydrogen;
(2) taken together and form a phthalimido group; or
(3) different and are either hydrogen or an amino-protecting group;
or a pharmaceutically-acceptable salt thereof.

2. A compound of claim 1, wherein $R_3$ and $R_4$ are hydrogen.

3. A compound of claim 2, wherein either $R_5$ or $R_6$ is hydrogen and the other is an amino-protecting group.

4. A compound of claim 3, wherein $R_2$ is a group of the formula

—$COOR_9$.

5. A compound of claim 4, wherein $R_9$ is methyl, ethyl, n-propyl or benzyl.

6. A compound of claim 5, wherein $R_1{}^a$ and $R_1{}^b$ are the same and are methyl and ethyl; and wherein either $R_5$ or $R_6$ is hydrogen and the other is a t-butoxycarbonyl group.

7. A compound of claim 3, wherein $R_2$ is a group of the formula

—$COR_8$.

8. A compound of claim 7, wherein $R_8$ is ethyl or monofluoromethyl.

9. A compound of claim 8, wherein $R_1{}^a$ and $R_1{}^b$ are the same and are methyl; and wherein either $R_5$ or $R_6$ is hydrogen and the other is a t-butoxycarbonyl group.

10. A compound of claim 3, wherein $R_2$ is cyano.

11. A compound of claim 10, wherein $R_1{}^a$ and $R_1{}^b$ are each ethyl; and wherein either $R_5$ or $R_6$ is hydrogen and the other is a t-butoxycarbonyl group.

12. A compound of claim 3, wherein $R_2$ is a group of the formula

13. A compound of claim 12, wherein $R_7$ is methyl and Z is 2.

14. A compound of claim 13, wherein $R_1{}^a$ and $R_1{}^b$ are each methyl; and wherein either $R_5$ or $R_6$ is hydrogen and the other is a t-butoxycarbonyl group.

15. A compound of claim 1 of the formula

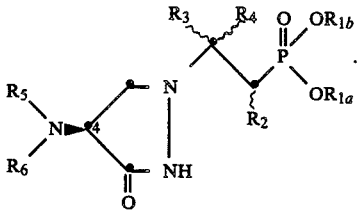

16. A compound of claim 15, wherein $R_3$ and $R_4$ are each hydrogen, and wherein either $R_5$ or $R_6$ is hydrogen and the other is an amino-protecting group.

17. A compound of claim 16, wherein $R_2$ is cyano.

18. A compound of claim 17, wherein $R_1{}^a$ and $R_1{}^b$ are each ethyl; and wherein either $R_5$ or $R_6$ is hydrogen and the other is a t-butoxycarbonyl group.

* * * * *

UNITED STATES PATENT AND TRADEMARK OFFICE
CERTIFICATE OF CORRECTION

PATENT NO. : 4,716,232

DATED : December 29, 1987

INVENTOR(S) : Robert J. Ternansky

It is certified that error appears in the above—identified patent and that said Letters Patent is hereby corrected as shown below:

Column 45, line 59, "$R_1^a$ and $R_1^b$" should read -- $R_{1a}$ and $R_{1b}$ --.

Column 46, line 6, "maybe" should read -- may be --; line 20, "-thaizol-" should read -- -thiazol- --; line 25, "-triazxol-" should read -- -triazol- --; line 26, "-oxazxol-" should read -- -oxazol- --; line 31, "thaidiazol-" should read -- thiadiazol- --; line 39, "-trazol-" should read -- -triazol- -- line 45, "-trazin-" should read -- -triazin- --; line 48, "-trazin-" should read -- -triazin----; line 54, "-dihydro5-" should read -- -dihydro-5- --; line 55, "triazxin-" should read -- triazin- --; line 56, "8-aminotetrazxolo" should read -- 8-aminotetrazolo --.

Column 47, line 40, "N-(methylsulfonyamino)" should read -- N-(methylsulfonylamino) --; line 42, "-thadiazol-" should read -- -thiadiazol- -- line 44, "2-hydroxy-1,3,4-triazol-5-yl-" should read -- 2-hydroxy-1,3,4-triazol-5-yl, --; line 45, "-2-(protected" should read -- 2-(protected --; line 59, "-triazxol-" should read -- -triazol- --; line 60, "-triazxol-" should read -- -triazol- --; line 64, delete "b".

Column 48, line 4, "-trizin-" should read -- -triazin- --; line 7, "$[1,5]$" should read -- $[1,5-b]$ --; line 11, "eth-  2-yl)-" should read -- eth-2-yl)- --; line 19, "-2methyl-" should read -- -2-methyl- --; line 20, "tetrazxolo" should read -- tetrazolo --; line 45, "or a" should read -- or an --; line 48, "hydroy," should read -- hydroxy --; line 53, "N-(methulsul-" should read -- N-(methylsul- --.

Column 49, line 12, "proteocted" should read -- protected --; line 21, "$c_1$" should read -- $C_1$ --; line 24, "logne," should read -- logen, --; line 32, "hyddroxy," should read -- hydroxy, --; line 37, "carboxy -protecting" should read -- carboxy-protecting --.

Column 50, line 11, "oxdiazol-" should read -- oxadiazol- --; line 13, "-1,3,4- thiadia-" should read -- -1,3,4-thiadia- --; line 22, "1,2,3,-" should read -- 1,2,3- --; line 24, "-triazxol-" should read -- -triazol- --; line 31, "dro- 5-" should read -- dro-5- --; line 45, insert before "sodium" -- 1-(methylsulfonic acid)-1H-tetrazol-5-yl --.

UNITED STATES PATENT AND TRADEMARK OFFICE
CERTIFICATE OF CORRECTION

PATENT NO. : 4,716,232

DATED : December 29, 1987

INVENTOR(S) : Robert J. Ternansky

It is certified that error appears in the above—identified patent and that said Letters Patent is hereby corrected as shown below:

Column 51, line 12, "aminoethyl," should read -- aminomethyl, --; line 36, "$R_1^a$ and $R_1^b$" should read -- $R_{1a}$ and $R_{1b}$ --.

Column 52, line 5, "$R_1^a$ and $R_1^b$" should read -- $R_{1a}$ and $R_{1b}$ --; line 9, "$R_1^a$ and $R_1^b$" should read -- $R_{1a}$ and $R_{1b}$ --; line 20, "$R_1^a$ and $R_1^b$" should read -- $R_{1a}$ and $R_{1b}$ --; line 39, "$R_1^a$ and $R_1^b$" should read -- $R_{1a}$ and $R_{1b}$ --.

Signed and Sealed this

Twentieth Day of September, 1988

Attest:

DONALD J. QUIGG

Attesting Officer

Commissioner of Patents and Trademarks